US012016863B2

(12) United States Patent
Plemper et al.

(10) Patent No.: US 12,016,863 B2
(45) Date of Patent: Jun. 25, 2024

(54) INHIBITORS OF RSV REPLICATION AND APPLICATIONS THEREOF

(71) Applicants: GEORGIA STATE UNIVERSITY RESEARCH FOUNDATION, INC., Atlanta, GA (US); EMORY UNIVERSITY, Atlanta, GA (US)

(72) Inventors: Richard Plemper, Atlanta, GA (US); Julien Sourimant, Atlanta, GA (US); Edgars Jecs, Decatur, GA (US); Dennis Liotta, Atlanta, GA (US); Stephen Pelly, Atlanta, GA (US); Robert Wilson, Ganesvoort, NY (US); Zackery Will Dentmon, East Point, GA (US)

(73) Assignees: Georgia State University Research Foundation, Inc., Atlanta, GA (US); Emory University, Atlanta, GA (US)

( * ) Notice: Subject to any disclaimer, the term of this patent is extended or adjusted under 35 U.S.C. 154(b) by 816 days.

(21) Appl. No.: 17/052,595

(22) PCT Filed: May 3, 2019

(86) PCT No.: PCT/US2019/030675
§ 371 (c)(1),
(2) Date: Nov. 3, 2020

(87) PCT Pub. No.: WO2019/213579
PCT Pub. Date: Nov. 7, 2019

(65) Prior Publication Data
US 2021/0244740 A1   Aug. 12, 2021

Related U.S. Application Data

(60) Provisional application No. 62/666,411, filed on May 3, 2018.

(51) Int. Cl.
| | | |
|---|---|---|
| C07D 487/04 | (2006.01) | |
| A61K 31/353 | (2006.01) | |
| A61K 31/519 | (2006.01) | |
| A61K 47/60 | (2017.01) | |
| A61P 31/14 | (2006.01) | |
| C07D 311/16 | (2006.01) | |
| C07D 311/18 | (2006.01) | |

(52) U.S. Cl.
CPC .......... *A61K 31/519* (2013.01); *A61K 31/353* (2013.01); *A61K 47/60* (2017.08); *A61P 31/14* (2018.01); *C07D 311/16* (2013.01); *C07D 311/18* (2013.01); *C07D 487/04* (2013.01)

(58) Field of Classification Search
CPC ..... C07D 487/04; A61K 31/41; A61K 31/519
See application file for complete search history.

(56) References Cited

U.S. PATENT DOCUMENTS

2014/0038988 A1   2/2014 Von Nussbaum et al.

FOREIGN PATENT DOCUMENTS

| WO | 2012/080451 A1 | 6/2012 |
| WO | 2016/174079 A1 | 11/2016 |

OTHER PUBLICATIONS

Zeng et al., CAPLUS Abstract 156:257710 (2012).*
International Search Report and Written Opinion issued in PCT/US2019/030675, dated Aug. 19, 2019, 12 pages.
Pubchem, Substance Record for SID 333275428. Available Date: Apr. 13, 2017. [retrieved on Jun. 6, 2019]. Retrieved from the Internet <https://pubchem.ncbi.nlm.nih.gov/substance/333275428>.
Pubchem, Substance Record for SID 329830955. Available Date: Mar. 3, 2017. [retrieved on Jun. 6, 2019]. Retrieved from the Internet: <https://pubchem.ncbi.nlm.nih.gov/substance/329830955>.
Rasputin, Nikolay A. et al. "Direct (het)arylation of [1,2,4]triazolo[1,5-a] pyrimidines: Both eliminative and oxidative pathways," Tetrahedron, vol. 73, No. 37, Sep. 1, 2017 (Sep. 1, 2017), pp. 5500-5508.
Chebanov, Valentin et al. "Three-Component Procedure for the Synthesis of 5-Aryl-5,8-dihydroazolo[1,5-a]pyrimidine-7-carboxylic Acids," Synthesis, vol. 2005, No. 15, Jul. 18, 2005 (Jul. 18, 2005), pp. 2597-2601.
Gein, V. L. et al. "Synthesis of alkyl 7-aryl-6-aroyl-4,7-dihydrotetrazolo[1,5-a]pyrimidine-5-carboxylates," Russian Journal of General Chemistry., vol. 85, No. 10, Oct. 1, 2015 (Oct. 1, 2015), pp. 2299-2303.
Katsori, Anna-Maria et al. "Coumarin derivatives: an updated patent review (2012-2014)," Expert Opinion on Therapeutic Patents, vol. 24, No. 12, Oct. 18, 2014 (Oct. 18, 2014), pp. 1323-1347.
Casasanta, Michael A. et al. "A chemical and biological toolbox for Type Vd secretion: Characterization of the phospholipase A1 autotransporter Fp1A from Fusobacterium nucleatum," Journal of Biological Chemistry, vol. 292, No. 49, Dec. 1, 2017 (Dec. 1, 2017), pp. 20240-20254.
Zhuang, Huan et al. "Copper(I)-Catalyzed 3-Position Methylation of Coumarins by Using Di-tert-butyl Peroxide as the Methylation Reagents," Chinese Journal of Chemistry, vol. 34, No. 4, Mar. 14, 2016 (Mar. 14, 2016) , pp. 368-372.
Gao, Xiang et al. "Downregulation of Rubisco Activity by Non-enzymatic Acetylation of RbcL," Molecular Plant, vol. 9, No. 7, Jul. 1, 2016 (Jul. 1, 2016), pp. 1018-1027.
Extended European Search Report issued in corresponding EP application No. 19796614.6, dated Aug. 5, 2021, 11 pages.
Second Office Action dated Aug. 24, 2023, in Chinese Patent Application No. 201980042328.0.

(Continued)

*Primary Examiner* — Deepak R Rao
(74) *Attorney, Agent, or Firm* — Meunier Carlin & Curfman LLC

(57) ABSTRACT

Disclosed herein are compounds having antiviral activity, and, in particular, an inhibitory activity on the replication of Respiratory Syncytial Virus (RSV). Druggable target sites, including Px, in the RSV N protein are disclosed, as well as compounds targeting Px. The compounds can be used to treat patients with RSV infection.

9 Claims, 10 Drawing Sheets

(56) References Cited

OTHER PUBLICATIONS

Zeng et al. "Iodine-Catalyzed, Multicomponent, One-Pot Synthesis of 5-Aryl-5, 8-dihydrotetrazolo[1,5-a]pyrimidine-7-carboxylic Acids", Synthetic Communications, 41: 3635-3643 (2011).

\* cited by examiner

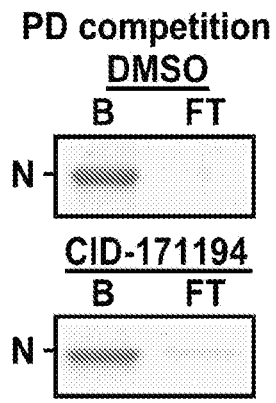
FIG. 10
| | |
|---|---|
| # compunds screened | 149051 |
| # >40% activity >3 robust Z-score | 319 |
| # passes orthog. counter | 13 |
| # distinct scaffolds | 8 |
| coefficient of variation | 7.84 |
| signal to background | 10.71 |
| Z'-factor | 0.68 |
FIG. 11
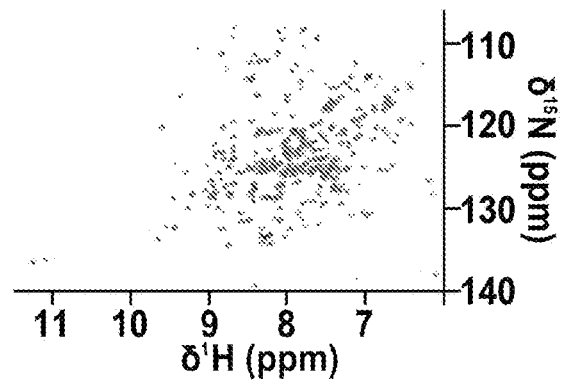
FIG. 12

INHIBITORS OF RSV REPLICATION AND APPLICATIONS THEREOF

CROSS-REFERENCE TO RELATED APPLICATION

This is a national stage application filed under 35 U.S.C. § 371 of PCT International Application No. PCT/US2019/030675, filed on May 3, 2019, entitled "Inhibitors of RSV Replication and Applications Thereof," which claims the benefit of U.S. Provisional Application 62/666,411, filed on May 3, 2018, the contents of which are hereby incorporated in their entireties its.

STATEMENT OF GOVERNMENT SUPPORT

This invention was made with government support under Grant no. A1071002 awarded by the National Institutes of Health and National Institute of Allergy and Infectious Diseases. The government has certain rights in the invention.

TECHNICAL FIELD

The present disclosure relates to compounds having antiviral activity, and, in particular, an inhibitory activity on the replication of Respiratory Syncytial Virus (RSV). It further relates to methods for preparing these compounds, pharmaceutical compositions comprising these compounds and uses thereof for the treatment and prevention of RSV infection.

BACKGROUND

Respiratory Syncytial Virus (RSV) is a single stranded, negative sense RNA virus of the pneumovirus family that was first discovered in 1956. It causes upper and lower respiratory tract infections and infects 60% of infants in their first viral season. It will have infected nearly all children by 2-3 years of age. Of those infected by RSV, approximately 3% will develop an infection severe enough to warrant hospitalization. However, RSV infection is not only a problem for the young; its substantial threat to the health especially of the elderly and the immunocompromised is increasingly recognized.

There are some drugs available for use against RSV infection. One such drug is Virazole® an aerosol form of ribavirin, a nucleoside analogue, which can be used for the treatment of serious RSV infection in hospitalized children. The aerosol route of administration, the toxicity (risk of teratogenicity), the cost and the highly variable efficacy, however, limit its use. Two other drugs, RespiGam® (RSV-IG) and Synagis® (palivizumab) are polyclonal and monoclonal antibodies, respectively, that are used for immunoprophylaxis to prevent infection. However, both are expensive, limiting their use to high risk infants in the developed world. Furthermore, palivizumab is not effective in the treatment of established RSV infection. A newer version monoclonal antibody, motavizumab, designed as a potential replacement of palivizumab, failed to show additional benefits in recent Phase III clinical trials.

There is thus a major unmet medical need for safe and effective therapeutics capable of both treating active RSV infections for improved case management and being administered prophylactically to prevent infection.

SUMMARY

Disclosed herein are compounds having the formula:

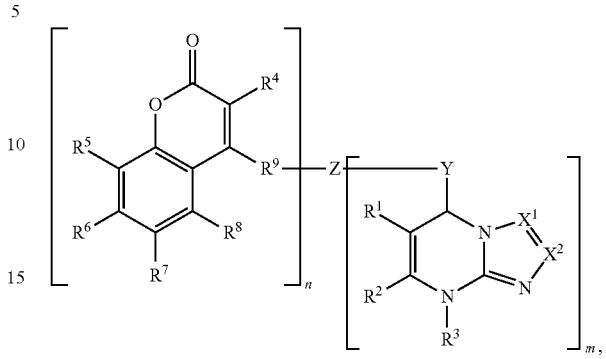

or a pharmaceutically acceptable salt thereof,
wherein n is 1 or 0 and m is 1 or 0, provided that at least one of n or m is 1;
Z is a linking moiety when n and m are each 1, and absent when either n or m is 0;
$X^1$ is selected from N and $CR^{x1}$, wherein $R^{x1}$ is selected from $R^{xx1}$, $OR^{xx1}$, $N(R^{xx1})_2$, $SiR^{xx1}_3$, $SR^{xx1}$, $SO_2R^{xx1}$, $SO_2N(R^{xx1})_2$, $C(O)R^{xx1}$; $C(O)OR^{xx1}$, $OC(O)R^{xx1}$; $(NR^{xx1})C(O)OR^{xx1}$, $C(O)N(R^{xx1})_2$, $C(O)N(OR^{xx1})(R^{xx1})$, $OC(O)N(R^{xx1})_2$, $N(R^{xx1})C(O)R^{xx1}$, $N(R^{xx1})C(O)N(R^{xx1})_2$, F, Cl, Br, I, cyano, and nitro, wherein $R^{xx1}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
$X^2$ is selected from N and $CR^{x2}$, wherein $R^{x2}$ is selected from $R^{xx2}$, $OR^{xx2}$, $N(R^{xx2})_2$, $SiR^{xx2}_3$, $SR^{xx2}$, $SO_2R^{xx2}$, $SO_2N(R^{xx2})_2$, $C(O)R^{xx2}$; $C(O)OR^{xx2}$, $OCOR^{xx2}$; $C(O)N(R^{xx2})_2$, $(NR^{xx2})C(O)OR^{xx2}$, $C(O)N(OR^{xx2})(R^{xx2})$, $OC(O)N(R^{xx2})_2$, $N(R^{xx2})C(O)N(R^{xx2})_2$, $N(R^{xx2})C(O)R^{xx2}$, F, Cl, Br, I, cyano, and nitro, wherein $R^{xx2}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
Y is selected from $C_{1-8}$alkyl, $C_{2-8}$alkenyl, $C_{2-8}$alkynyl, aryl, $C_{1-8}$heteroaryl, $C_{3-8}$cycloalkyl, or $C_{i-}$ heterocyclyl;
$R^1$ is selected from $R^{1a}$, $OR^{1a}$, $N(R^{1a})_2$, $SiR^{1a}_3$, $SR^{1a}$, $SO_2R^{1a}$, $SO_2N(R^{1a})_2$, $C(O)R^{1a}$; $C(O)OR^{1a}$, $OCOR^{1a}$; $C(O)N(R^{1a})_2$, $(NR^{1a})C(O)OR^{1a}$, $C(O)N(OR^{1a})(R^{1a})$, $OC(O)N(R^{1a})_2$, $N(R^{1a})C(O)N(R^{1a})_2$, $N(R^{1a})C(O)R^{1a}$, F, Cl, Br, I, cyano, and nitro, wherein $R^{1a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
$R^2$ is selected from $R^{2a}$, $OR^{2a}$, $N(R^{2a})_2$, $SiR^{2a}_3$, $SR^{2a}$, $SO_2R^{2a}$, $SO_2N(R^{2a})_2$, $C(O)R^{2a}$; $C(O)OR^{2a}$, $OCOR^{2a}$; $(NR^{2a})C(O)OR^{2a}$, $C(O)N(R^{2a})_2$, $C(O)N(OR^{2a})(R^{2a})$, $OC(O)N(R^{2a})_2$, $N(R^{2a})C(O)N(R^{2a})_2$, $N(R^{2a})C(O)R^{2a}$, F, Cl, Br, I, cyano, and nitro, wherein $R^{2a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;
$R^3$ is selected from $R^{3a}$, $SO_2R^{3a}$, $SO_2N(R^{3a})_2$, $C(O)R^{3a}$; $C(O)OR^{3a}$, $C(O)N(R^{3a})_2$, $C(O)N(OR^{3a})(R^{3a})$, wherein $R^{3a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^4$ is selected from $R^{4a}$, $OR^{4a}$, $N(R^{4a})_2$, $SiR^{4a}_3$, $SR^{4a}$, $SO_2R^{4a}$, $SO_2N(R^{4a})_2$, $C(O)R^{4a}$; $C(O)OR^{4a}$, $OCOR^{4a}$; $(NR^{4a})C(O)OR^{4a}$, $C(O)N(R^{4a})_2$, $C(O)N(OR^{4a})(R^{4a})$, $OC(O)N(R^{4a})_2$, $N(R^{4a})C(O)N(R^{4a})_2$, $N(R^{4a})C(O)R^{4a}$, F, Cl, Br, I, cyano, and nitro, wherein $R^{4a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^5$ is selected from $R^{5a}$, $OR^{5a}$, $N(R^{5a})_2$, $SiR^{5a}_3$, $SR^{5a}$, $SO_2R^{5a}$, $SO_2N(R^{5a})_2$, $C(O)R^{5a}$; $C(O)OR^{5a}$, $OCOR^{5a}$; $(NR^{5a})C(O)OR^{5a}$, $C(O)N(R^{5a})_2$, $C(O)N(OR^{5a})(R^{5a})$, $OC(O)N(R^{5a})_2$, $N(R^{5a})C(O)N(R^{5a})_2$, $N(R^{5a})C(O)R^{5a}$, F, Cl, Br, I, cyano, and nitro, wherein $R^{5a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^6$ is selected from $R^{6a}$, $OR^{6a}$, $N(R^{6a})_2$, $SiR^{6a}_3$, $SR^{6a}$, $SO_2R^{6a}$, $SO_2N(R^{6a})_2$, $C(O)R^{6a}$; $C(O)OR^{6a}$, $OCOR^{6a}$; $C(O)N(R^{6a})_2$, $C(O)N(OR^{6a})(R^{6a})$, $OC(O)N(R^{6a})_2$, $N(R^{6a})C(O)N(R^{6a})_2$, $N(R^{6a})C(O)R^{6a}$, F, Cl, Br, I, cyano, and nitro, wherein $R^{6a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^8$ is selected from $R^{7a}$, $N(R^{7a})_2$, $SiR^{7a}_3$, $SR^{7a}$, $SO_2R^{7a}$, $SO_2N(R^{7a})_2$, $C(O)R^{7a}$; $C(O)OR^{7a}$, $OCOR^{7a}$, $C(O)N(R^{7a})_2$, $C(O)N(OR^{7a})(R^{7a})$, $OC(O)N(R^{7a})_2$, $N(R^{7a})C(O)N(R^{7a})_2$, $N(R^{7a})C(O)R^{7a}$, F, Cl, Br, I, cyano, and nitro, wherein $R^{7a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^8$ is selected from $R^{8a}$, $OR^{8a}$, $N(R^{8a})_2$, $SiR^{8a}_3$, $SR^{8a}$, $SO_2R^{8a}$, $SO_2N(R^{8a})_2$, $C(O)R^{8a}$; $C(O)OR^{8a}$, $OCOR^{8a}$; $C(O)N(R^{8a})_2$, $C(O)N(OR^{8a})(R^{8a})$, $OC(O)N(R^{8a})_2$, $N(R^{8a})C(O)N(R^{8a})_2$, $N(R^{8a})C(O)R^{8a}$, F, Cl, Br, I, cyano, and nitro, wherein $R^{8a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein when Z is a linking moiety, then $R^9$ is absent;

when m is O, $R^9$ is selected from $R^{9a}$, $OR^{9a}$, $N(R^{9a})_2$, $SiR^{9a}_3$, $SR^{9a}$, $SO_2R^{9a}$, $SO_2N(R^{9a})_2$, $C(O)R^{9a}$; $C(O)OR^{9a}$, $OCOR^{9a}$; $C(O)N(R^{9a})_2$, $C(O)N(OR^{9a})(R^{9a})$, $OC(O)N(R^{9a})_2$, $N(R^{9a})C(O)N(R^{9a})_2$, $N(R^{9a})C(O)R^{9a}$, F, Cl, Br, I, cyano, and nitro, wherein $R^{9a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl.

In some instances, the compound can have the formula:

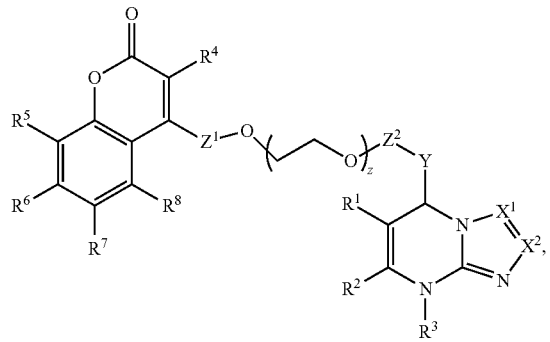

wherein $X^1$, $X^2$, $R^1$, $R^2$, $R^3$, $R^4$, $R^5$, $R^6$, $R^7$, $R^8$ and Y have the meanings given above;

z is an integer from 1-10;

$Z^1$ is selected from a chemical bond, $C_{1-8}$alkyl, $C_{2-8}$alkenyl, $C_{2-8}$alkynyl, $-(CH_2)_a-OC(O)-(CH_2)_{a'}-C(O)-$, wherein a is selected from 0-4, and a' is selected from 1-4; and $Z^2$ is selected from a chemical bond, $C_{1-8}$alkyl, $C_{2-8}$alkenyl, $C_{2-8}$alkynyl, $-(CH_2)_b-OC(O)-(CH_2)_{b'}-C(O)-$, wherein b is selected from 0-4, and b' is selected from 1-4.

In certain instances, the compounds have the formula:

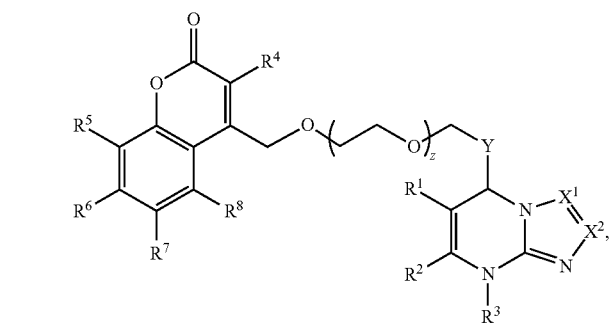

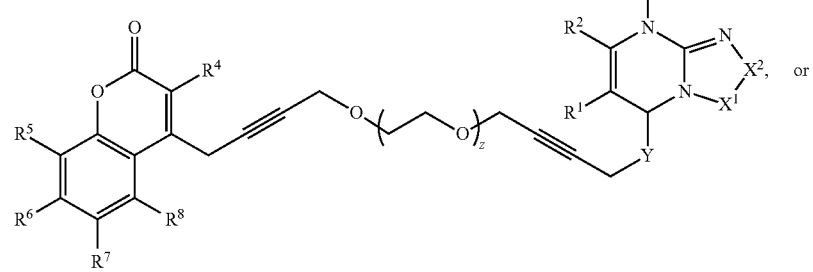

-continued

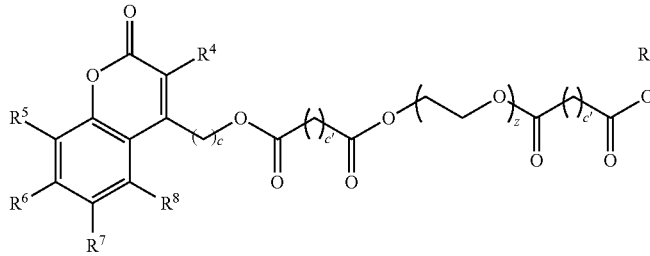

wherein c is independently selected from 0-4, and c' is independently selected from 1-4.

Preferred Y groups include phenyl, for instance having the formula:

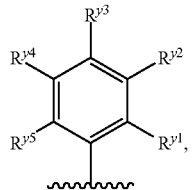

wherein $R^{y1}$, $R^{y2}$, $R^{y3}$, $R^{y4}$, and $R^{y5}$ are independently selected from $R^{ya}$, $OR^{ya}$, $N(R^{ya})_2$, $SiR^{ya}_3$, $SR^{ya}$, $SO_2R^{ya}$, $SO_2N(R^{ya})_2$, $C(O)R^{1a}$; $C(O)OR^{ya}$, $OCOR^{ya}$; $C(O)N(R^{ya})_2$, $C(O)N(OR^{ya})(R^{ya})$, $OC(O)N(R^{ya})_2$, $N(R^{ya})C(O)N(R^{ya})_2$, $N(R^{ya})C(O)NR^{ya}$, F, Cl, Br, I, cyano, and nitro, wherein $R^{ya}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl, with the proviso that when n and m are each 1, one of $R^{y1}$, $R^{y2}$, $R^{y3}$, $R^{y4}$, and $R^{y5}$ represents a bond to Z.

In some instances $R^{y2}$, $R^{y3}$, $R^{y4}$ are each hydrogen, and $R^{5y}$ represents a bond to Z when n and m are each 1, and $R^{5y}$ is hydrogen when is n 0. Preferably, $R^{y1}$ is selected from $OR^{ya}$, F, Cl, Br, I, cyano, and nitro.

In certain embodiments, X 1 and X 2 are both N.

Also disclosed are compounds having the formula:

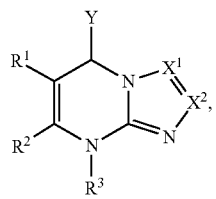

or a pharmaceutically acceptable salt thereof,
wherein:

$X^1$ is selected from N and $CR^{x1}$, wherein $R^{x1}$ is selected from $R^{xx1}$, $OR^{xx1}$, $N(R^{xx1})_2$, $SiR^{xx1}_3$, $SR^{xx1}$, $SO_2R^{xx1}$, $SO_2N(R^{xx1})_2$, $C(O)R^{xx1}$; $C(O)OR^{xx1}$, $OCOR^{xx1}$; $C(O)N(R^{xx1})_2$; $C(O)N(OR^{xx1})(R^{xx1})$, $OC(O)N(R^{xx1})_2$, $N(R^{xx1})C(O)N(R^{xx1})_2$, $N(R^{xx1})C(O)R^{xx1}$, F, Cl, BR I, cyano, and nitro, wherein $R^{xx1}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$X^2$ is selected from N and $CR^{x2}$, wherein $R^{x2}$ is selected from $R^{xx2}$, $OR^{xx2}$, $N(R^{xx2})_2$, $SiR^{xx2}_3$, $SR^{xx2}$, $SO_2R^{xx2}$, $SO_2N(R^{xx2})_2$, $C(O)R^{xx2}$; $C(O)OR^{xx2}$; $OCOR^{xx2}$; $C(O)N(R^{xx2})_2$, $C(O)N(OR^{xx2})(R^{xx2})$, $OC(O)N(R^{xx2})_2$, $N(R^{xx2})C(O)N(R^{xx2})_2$, $N(R^{xx2})C(O)R^{xx2}$, F, Cl, Br, I, cyano, and nitro, wherein $R^{xx2}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

Y is selected from $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^1$ is selected from $R^{1a}$, $OR^{1a}$, $N(R^{1a})_2$, $SiR^{1a}_3$, $SR^{1a}$, $SO_2R^{1a}$, $SO_2N(R^{1a})_2$, $C(O)R^{1a}$; $C(O)OR^{1a}$, $OCOR^{1a}$; $C(O)N(R^{1a})_2$, $C(O)N(OR^{1a})(R^{1a})$, $OC(O)N(R^{1a})_2$, $N(R^{1a})C(O)N(R^{1a})_2$, $N(R^{1a})C(O)R^{1a}$, F, Cl, Br, I, cyano, and nitro, wherein $R^{1a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^2$ is selected from $R^{2a}$, $OR^{2a}$, $N(R^{2a})_2$, $SiR^{2a}_3$, $SR_{2a}$, $SO_2R^{2a}$, $SO_2N(R2^a)_2$, $C(O)R^{2a}$; $C(O)OR^{2a}$, $OCOR^{2a}$; $C(O)N(R^{2a})_2$, $C(O)N(OR^{2a})(R^{2a})$, $OC(O)N(R^{2a})_2$, $N(R^{2a})C(O)N(R^{2a})_2$, $N(R^{2a})C(O)R^{2a}$, F, Cl, Br, I, cyano, and nitro, wherein $R^{2a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^3$ is selected from $R^{3a}$, $SO_2R^{3a}$, $SO_2N(R^{3a})_2$, $C(O)R^{3a}$; $C(O)OR^{3a}$, $C(O)N(R^{3a})_2$, $C(O)N(OR^{3a})(R^{3a})$, wherein $R^{3a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

Preferred Y groups include phenyl, for instance:

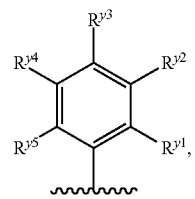

wherein $R^{y1}$, $R^{y2}$, $R^{y3}$, $R^{y4}$, and $R^{y5}$ are independently selected from $R^{ya}$, $OR^{ya}$, $N(R^{ya})_2$, $SiR^{ya}_3$, $SR^{ya}$, $SO_2R^{ya}$, $SO_2N(R^{ya})_2$, $C(O)R^{ya}$; $C(O)OR^{ya}$, $OCOR^{ya}$; $(NR^{ya})C(O)OR^{ya}$, $C(O)N(R^{ya})_2$, $C(O)N(OR^{ya})(R^{ya})$, $OC(O)N(R^{ya})_2$, $N(R^{ya})C(O)N(R^{ya})_2$, $N(R^{ya})C(O)R^{ya}$, F, Cl, Br, I, cyano, and nitro, wherein $R^{ya}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl. For these compounds, $X^1$ and $X^2$ can both be N, $R^1$ can be hydrogen, $R^2$ is $C(O)OR^{1a}$ or $C(O)N(R^{1a})_2$, in certain cases $R^2$ is $C(O)OR^{1a}$ and $R^{1a}$ is H or $C_{1-8}$alkyl. Exemplary $R^{1a}$ groups include H, isopropyl, 2,2,2-trifluoroethyl, ethyl, methyl, isobutyl. In certain instances, $R^{y1}$ is selected from F, Cl, Br, I, and $CF_3$.

Also disclosed are compounds having the formula:

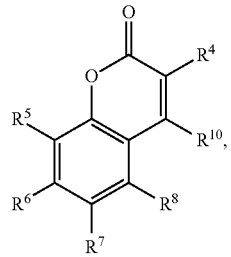

or a pharmaceutically acceptable salt thereof, wherein, $R^4$ is selected from $R^{4a}$, $OR^{4a}$, $N(R^{4a})_2$, $SiR^{4a}{}_3$, $SR^{4a}$, $SO_2R^{4a}$, $SO_2N(R^{4a})_2$, $C(O)R^{4a}$; $C(O)OR^{4a}$, $OCOR^{4a}$; $C(O)N(R^{4a})_2$, $C(O)N(OR^{4a})(R^{4a})$, $N(R^{4a})C(O)OR^{4a}$, $OC(O)N(R^{4a})_2$, $N(R^{4a})C(O)N(R^{4a})_2$, $N(R^{4a})C(O)R^{4a}$, F, Cl, Br, I, cyano, and nitro, wherein $R^{4a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^5$ is selected from $R^{5a}$, $OR^{5a}$, $N(R^{5a})_2$, $SiR^{5a}{}_3$, $SR^{5a}$, $SO_2R^{5a}$, $SO_2N(R^{5a})_2$, $C(O)R^{5a}$; $C(O)OR^{5a}$, $OCOR^5a$; $C(O)N(R^{5a})_2$, $C(O)N(OR^{5a})(R^{5a})$, $OC(O)N(R^{5a})_2$, $N(R^{5a})C(O)OR^{5a}$, $N(R^{5a})C(O)N(R^{5a})_2$, $N(R^{5a})C(O)R^{5a}$, F, Cl, Br, I, cyano, and nitro, wherein $R^{5a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^6$ is selected from $R^{6a}$, $OR^{6a}$, $N(R^{6a})_2$, $SiR^{6a}{}_3$, $SR^{6a}$, $SO_2R^{6a}$, $SO_2N(R^{6a})_2$, $C(O)R^{6a}$; $C(O)OR^{6a}$, $OCOR^6a$; $C(O)N(R^{6a})_2$, $C(O)N(OR\ 6a)(R6a)$, $OC(O)N(R^{6a})_2$, $N(R^{6a})C(O)OR^{6a}$, $N(R^{6a})C(O)N(R^{6a})_2$, $N(R^{6a})C(O)R^{6a}$, F, Cl, Br, I, cyano, and nitro, wherein $R^{6a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^7$ is selected from $R^{7a}$, $OR^{7a}$, $N(R^{7a})_2$, $SiR^{7a}{}_3$, $R^{7a}$, $SO_2R^{7a}$, $SO_2N(R^{7a})_2$, $C(O)R^{7a}$; $C(O)OR^{7a}$, $OCOR^7a$; $C(O)N(R^{7a})_2$, $C(O)N(OR^{7a})(R^{7a})$, $OC(O)N(R^{7a})_2$, $N(R^{7a})C(O)OR^{7a}$, $N(R^{7a})C(O)N(R^{7a})_2$, $N(R^{7a})C(O)R^{7a}$, F, Cl, Br, I, cyano, and nitro, wherein $R^{7a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^8$ is selected from $R^{8a}$, $OR^{8a}$, $N(R^{8a})_2$, $SiR^{8a}{}_3$, $SR^{8a}$, $SO_2R^{8a}$, $SO_2N(R^{8a})_2$, $C(O)R^{8a}$; $C(O)$01ea, $OCOR^8a$; $C(O)N(R^{8a})_2$, $C(O)N(OR^{8a})(R^{8a})$, $OC(O)N(R^{8a})_2$, $N(R^{8a})C(O)0R^{8a}$, $N(R^{8a})C(O)N(lea)_2$, $N(lea)C(O)lea$, F, Cl, Br, I, cyano, and nitro, wherein $R^{8a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^{10}$ is selected from $R^{10a}$, $OR^{10a}$, $N(R^{10a})_2$, $SiR^{10a}{}_3$, $SR^{10a}$, $SO_2R^{10a}$, $SO_2N(R^{10a})_2$, $C(O)R^{10a}$; $C(O)OR^{10a}$, $OCOR^{10a}$; $C(O)N(R^{10a})_2$, $C(O)N(OR^{10a})(R^{10a})$, $OC(O)N(R^{10a})_2$, $N(R^{10a})C(O)OR^{10a}$, $N(R^{10a})C(O)N(R^{10a})_2$, $N(R^{10a})C(O)R^{10a}$, F, Cl, Br, I, cyano, and nitro, wherein $R^{10a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl.

The compounds disclosed herein can be formulated into pharmaceutically acceptable compositions, as described herein, and can be administered to a patient infected with RSV, optionally in combination with one or more active agents.

A method of treating a patient infected with RSV, comprising administering the compound of any of claims 1-19 or the pharmaceutical composition of claim 20.

The method of claim 21, further comprising administering adjunctively at least one other active compound.

According to an embodiment of the present disclosure there is provided a compound according to Formula A or salt thereof, Formula A

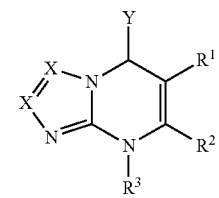

wherein $R^1$ is a H, halogen, aryl, heteroaryl or alkyl, and $R^1$ is optionally substituted with $R^{10}$; $R^2$ is a H, ester or carbamate, carboxylic acid, amide or hydroxamic acid, and $R^2$ is optionally substituted with $R^{10}$;

$R^3$ is H, alkyl, carbamate, amide, aryl, benzyl, heteroaryl or halogen, and $R^3$ is optionally substituted with $R^{10}$;

Each X is individually and independently N, CH, C-alkyl or C-halogen, and X is optionally substituted with $R^{10}$;

Y is an aryl, heteroaryl or alkyl, and Y is optionally substituted with $R^{10}$; and $R^{10}$ is an alkyl, aryl, heteroaryl, benzyl, carbamate, halogen or amide.

Further features of this embodiment provide for $R^2$ to be an ester of a methyl, ethyl, propyl, iso-propyl, butyl, iso-butyl, tent-butyl, benzyl or CH2CF3 group, or a corresponding amide which may be either mono- or di-substituted with the same or different groups; for $R^3$ to be a C1 to C6 alkyl which may be straight, branched, saturated, unsaturated or cyclic, a halogen, or an optionally substituted aryl or heteroaryl, all of which may be further optionally substituted with $R^{10}$; for both X groups to be N and for Y to be an aryl which is optionally substituted with a halogen, preferably in the ortho position. Some exemplary compounds of Formula A are

GRP-171194

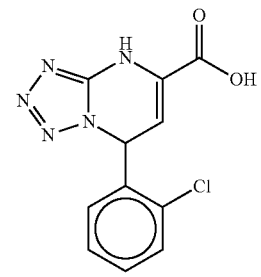

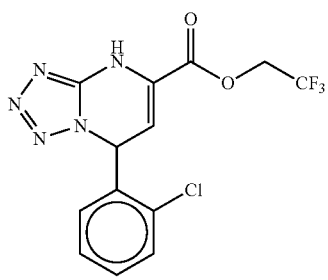

GRP-171194-1

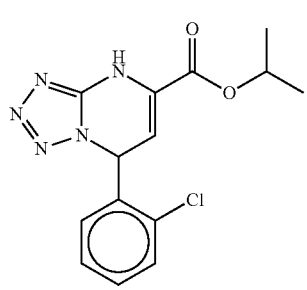

GRP-171194-2

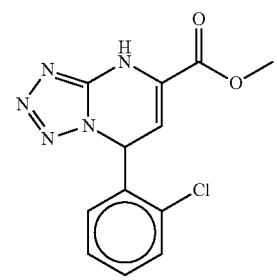

GRP-171194-3

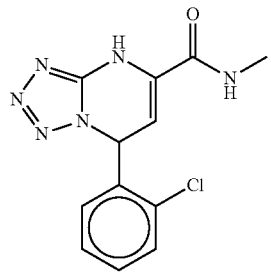

GRP-171194-4

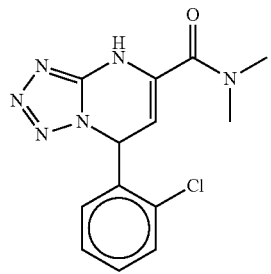

GRP-171194-5

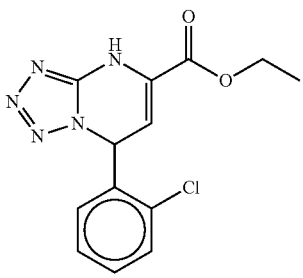

GRP-171194-5

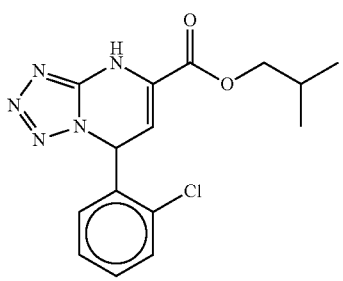

GRP-171194-6

According to another embodiment of the present disclosure there is provided a compound according to Formula B or salt thereof,

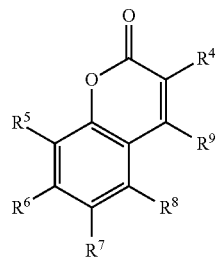

Formula B wherein $R^4$ is a H, aryl, amide, amino or a halogen and $R^4$ is optionally substituted with $R^{10}$; $R^5$, $R^6$, $R^7$, $R^8$ and $R^9$ are individually and independently a H, alkoxy, alkyl, halogen, aryl, heteroaryl, alkyl, amino, amide, ester or carbamate and $R^5$, $R^6$, $R^7$, $R^8$ and $R^9$ are individually and independently optionally substituted with $R^{10}$; and
$R^{10}$ is an alkyl, aryl, heteroaryl, benzyl, carbamate, halogen or amide.

Further features of this embodiment provide for $R^4$ to be a halogen such as Cl; for $R^5$ to be alkoxy such as methoxy, isopropyloxy, a mono or di-substitued carbamate wherein the substituents may be the same or different, an acetate, an ester of a methyl, ethyl, propyl, iso-propyl, butyl, iso-butyl, tent-butyl; and for $R^9$ to be a methyl, a C1 to C6 alkyl which may be straight, branched, saturated, unsaturated or cyclic, a halogen, or an optionally substituted aryl or heteroaryl. Some exemplary compounds of Formula B are

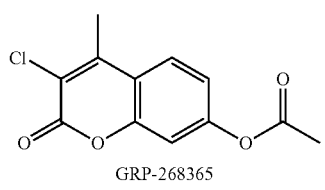

GRP-268365

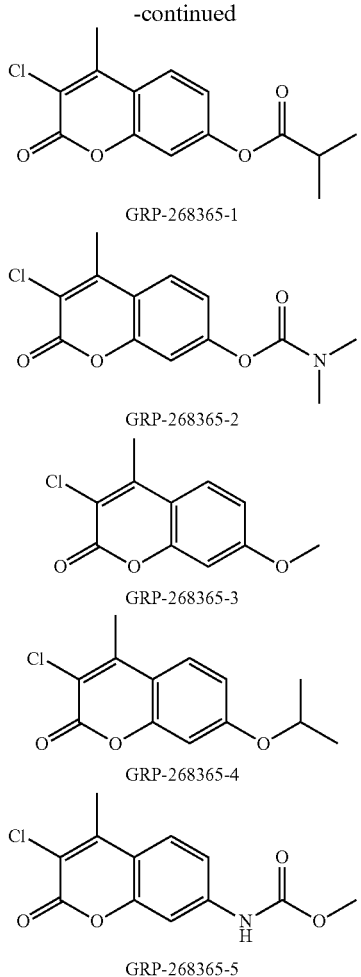

GRP-268365-1

GRP-268365-2

GRP-268365-3

GRP-268365-4

GRP-268365-5

According to yet another embodiment of the present disclosure there is provided a compound according to Formula C or salt thereof,

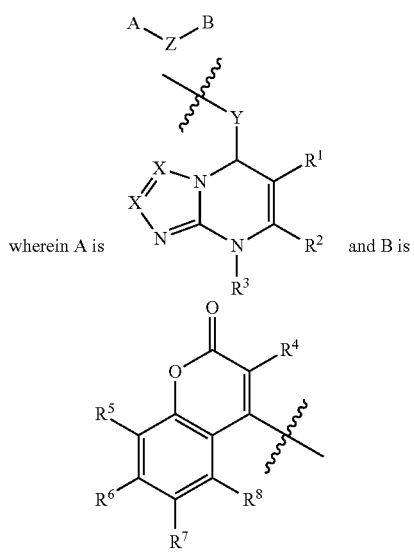

Formula C wherein A is and B is wherein $R^1$ is a H, halogen, aryl, heteroaryl or alkyl, and $R^1$ is optionally substituted with $R^{10}$; $R^2$ is a H, ester or carbamate, carboxylic acid, amide or hydroxamic acid, and $R^2$ is optionally substituted with $R^{10}$;

$R^3$ is H, alkyl, carbamate, amide, aryl, benzyl, heteroaryl or halogen, and $R^3$ is optionally substituted with $R^{10}$;

$R^4$ is a H, aryl, amide, amino or a halogen and $R^4$ is optionally substituted with $R^{10}$;

$R^5$, $R^6$, $R^7$, $R^8$ and $R^9$ are individually and independently a H, alkoxy, alkyl, halogen, aryl, heteroaryl, alkyl, amino, amide, ester or carbamate and $R^5$, $R^6$, $R^7$, $R^8$ and $R^9$ are individually and independently optionally substituted with $R^{10}$.

Each X is individually and independently N, CH, C-alkyl or C-halogen, and X is optionally substituted with $R^{10}$;

Y is an aryl, heteroaryl or alkyl, and Y is optionally substituted with $R^{10}$;

$R^{10}$ is an alkyl, aryl, heteroaryl, benzyl, carbamate, halogen or amide; and Z is an optionally substituted heterocarbon linking group which positions moieties A and B 16 to 20 Angstroms apart.

Further features provide for $R^1$ to be H, Cl, F, Br or I, for $R^2$ to be an ester of a methyl, ethyl, propyl, iso-propyl, butyl, iso-butyl, tent-butyl, benzyl or $CH_2CF_3$ group, or a corresponding amide which may be either mono- or di-substituted with the same or different groups; for $R^3$ to be a C1 to C6 alkyl which may be straight, branched, saturated, unsaturated or cyclic, a halogen, or an optionally substituted aryl or heteroaryl, all of which may be further substituted with $R^{10}$; for $R^4$ to be a halogen such as Cl; for $R^5$ to be alkoxy such as methoxy, isopropyloxy, a mono or di-substitued carbamate wherein the substituents may be the same or different, an acetate, an ester of a methyl, ethyl, propyl, iso-propyl, butyl, iso-butyl, tent-butyl; and for $R^9$ to be a methyl, a C1 to C6 alkyl which may be straight, branched, saturated, unsaturated or cyclic, a halogen, or an optionally substituted aryl or heteroaryl, for both X groups to be N and for Y to be an aryl which is optionally substituted with a halogen, preferably in the ortho position and for Z to be a heterocarbon linking group which is optionally substituted with one or more alkenes, alkynes, 3,5 substituted pyridines, pyrazoles, furans.

Z may be selected from the group consisting of:

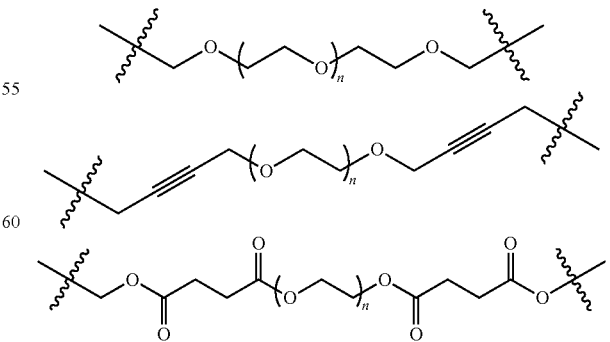

wherein n=3, 4, 5 or 6

Still further features of this embodiment provide for compounds of Formula C to be selected from
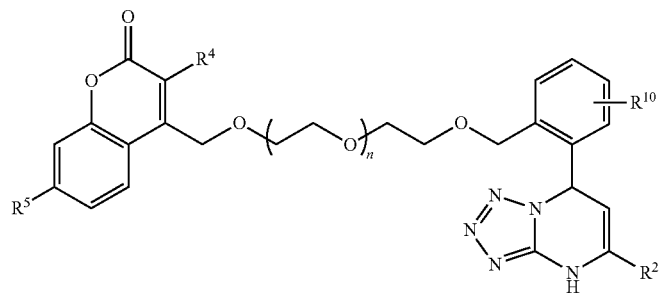
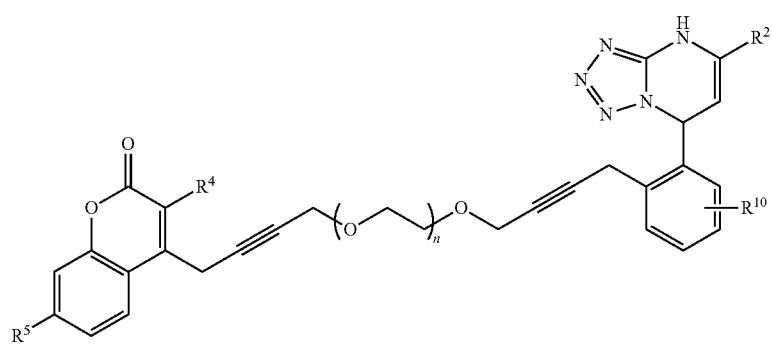
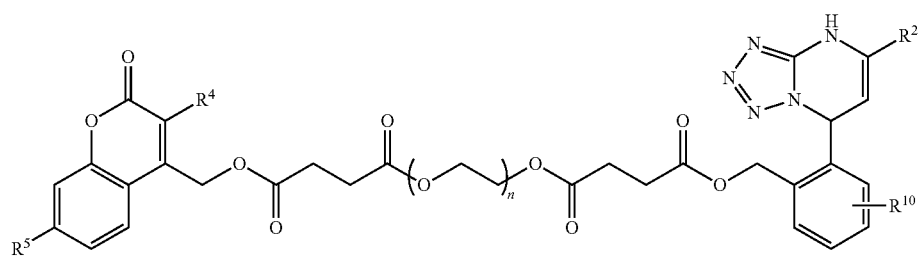
wherein $R^2$, $R^4$, $R^5$ and $R^{10}$ and n are as described above.
Some exemplary compounds of Formula C are
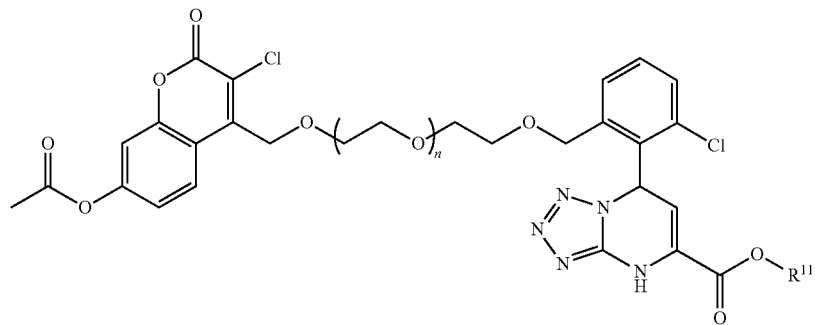

wherein n is as described above and $R^{11}$ is a methyl, ethyl, propyl, iso-propyl, butyl, iso-butyl, tent-butyl, benzyl or $CH_2CF_3$.

In a further embodiment, there is provided a newly identified druggable target site, designated Px, in the RSV N protein that is lined by residues Gly63, Leu64, Leu211, Val212, Lys215, and His216 (FIG. 20) and is involved in interaction of the RSV N and P proteins, and a method of identifying compounds useful in binding to that site, the method involving (i) providing a model comprising the druggable site, Px; (ii) providing one or more candidate inhibitor compounds potentially capable of targeting Px; (iii) evaluating contact between the candidate compounds and the residues in Px to determine which one of the candidate compounds have the ability to bind to and/or fit into Px, and (iv) identifying the compounds, which based on this evaluation, have the ability to bind to and/or fit in the Px site and are potentially useful for inhibiting RSV infection. In the method of identifying compounds that bind Px, the model may comprise a region of the N protein that surrounds and supports the native structure of the Px pocket.

In another aspect there is provided a method of treating RSV infection in a subject, the method comprising selecting a subject with the condition, proving a compound which binds to and/or fits the first model comprising the druggable target Px, and administering the compound to the selected subject under conditions effective to treat the RSV infection.

According to a further embodiment there is provided compounds of Formula (E) or salts thereof for use in the treatment of RSV.

-continued

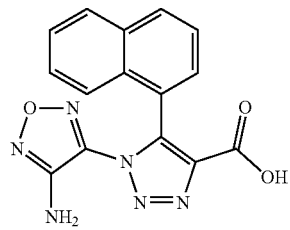
GRP-154928

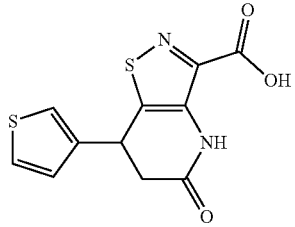
GRP-242487

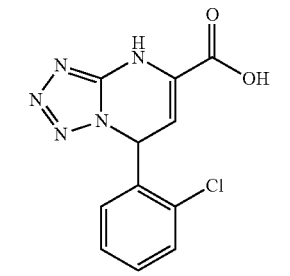
GRP-171194

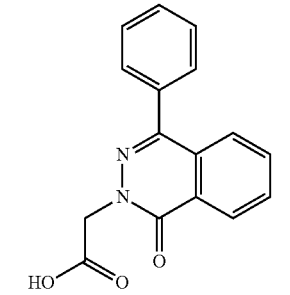
GRP-268695

In another embodiment there is provided a method of treating RSV in a subject in need thereof, the method comprising administering an effective amount of the compound of Formula A, Formula B, Formula C or Formula E, or salts thereof to the subject.

In certain embodiments, the disclosure contemplates derivatives of compounds disclosed herein such as those containing one or more, the same or different, substituents.

In still another embodiment there is provided a pharmaceutical composition comprising a compound of Formula A, Formula B, Formula C or Formula E or salts thereof and a pharmaceutically acceptable excipient. In certain embodiments, the pharmaceutical composition is in the form of a tablet, capsule, pill, gel, granules, aerosol, or aqueous buffer, such as a saline or phosphate buffer, or a nanoparticle formulation, emulsion, liposome, etc. The pharmaceutical composition may also include one or more further antiviral agents or may be administered in combination with one or more such active agent.

In a yet further embodiment there is provided methods for preparing the compounds of Formula A, Formula B, Formula C or Formula E, or salts thereof comprising mixing one or more starting materials with reagents under conditions such that the products are formed.

BRIEF DESCRIPTION OF THE DRAWINGS

FIG. 10 is a pull-down of purified RSV N with GST-tagged Pin presence of compound (300 µM) or vehicle (DMSO equivalent). Affinity-precipitated material (AP) and flow-through (FT) analyzed by SDS-PAGE and Coomassie stain. Only in the presence of compound is free N material detectable in FT;

FIG. 11 shows a summary of campaign performance and hit analysis pipeline;

FIG. 12 shows an overlay of $^1H^{15}$ N HSQC spectra of $N_{[31-252]}$ in presence of 1% DMSO superimposed on the spectra. High similarity enabled retrieving 95% of assigned residues;

FIG. 14 is a surface representation of RSV $N_{[31-252]}$ generated by APBS for Pymol (PDB: 4ucd). GRP-171194 and −268365 shown by $^1H^{15}N$ HSQC and SAMPLEX analysis to dock into two discrete sites (P1, left arrow; Px, right arrow). Molecular docking was performed and refined with the Molecular Operating Environment (MOE) software package (Chemical Computing Group), and the best poses rescored using experimental HN CSPs by HECSP and NMRscore_P algorithms;

Figure 15:
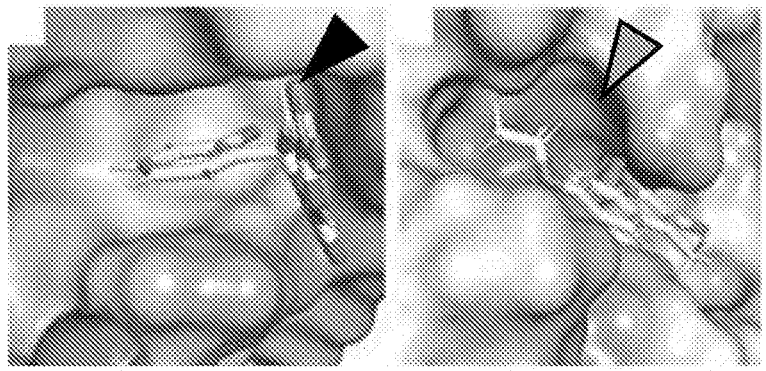

FIG. 15 shows top-scoring poses are consistent with observed CSPs for GRP-171191 and GRP-268365.

Figure 16:
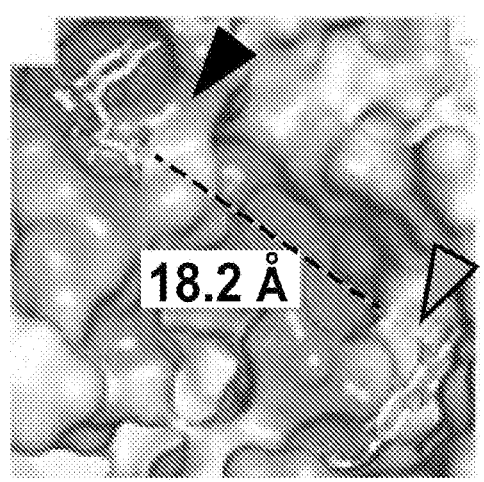
Figure 17:
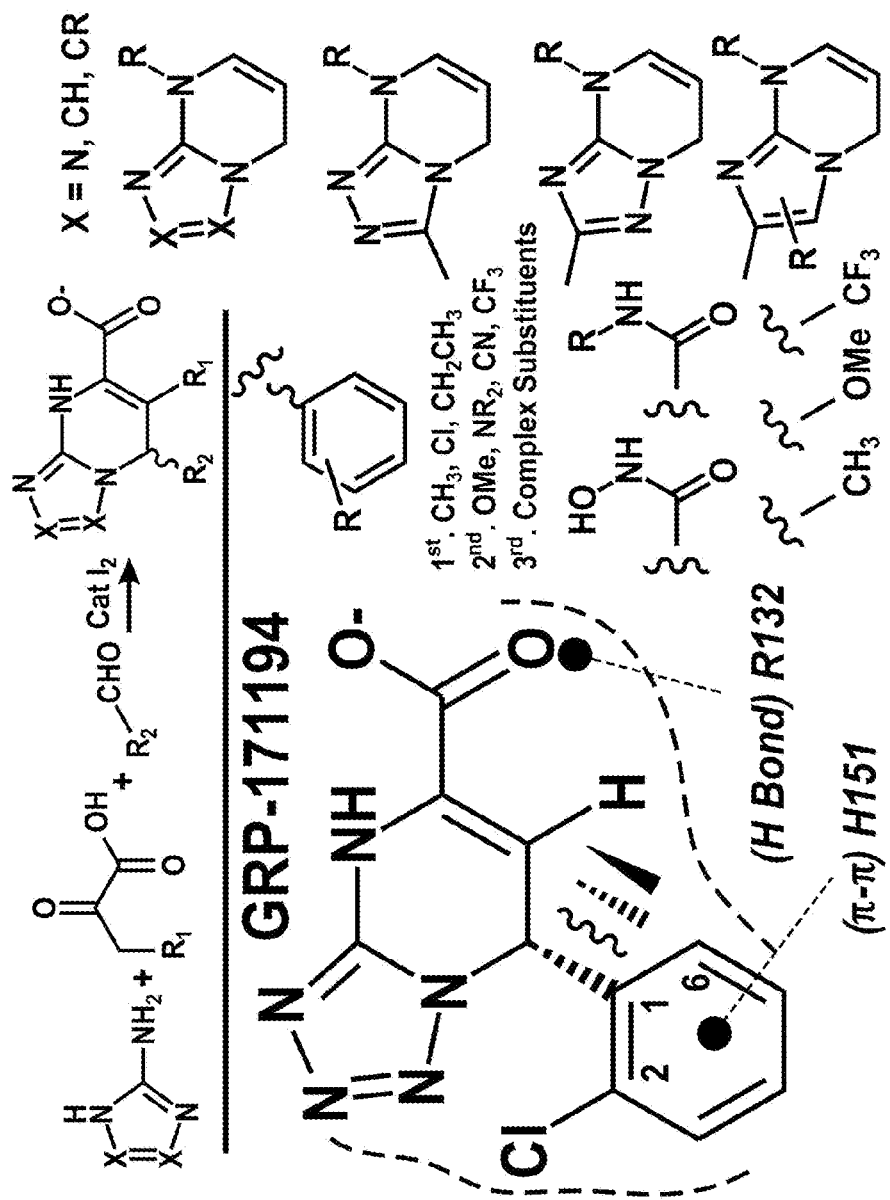
Figure 18:
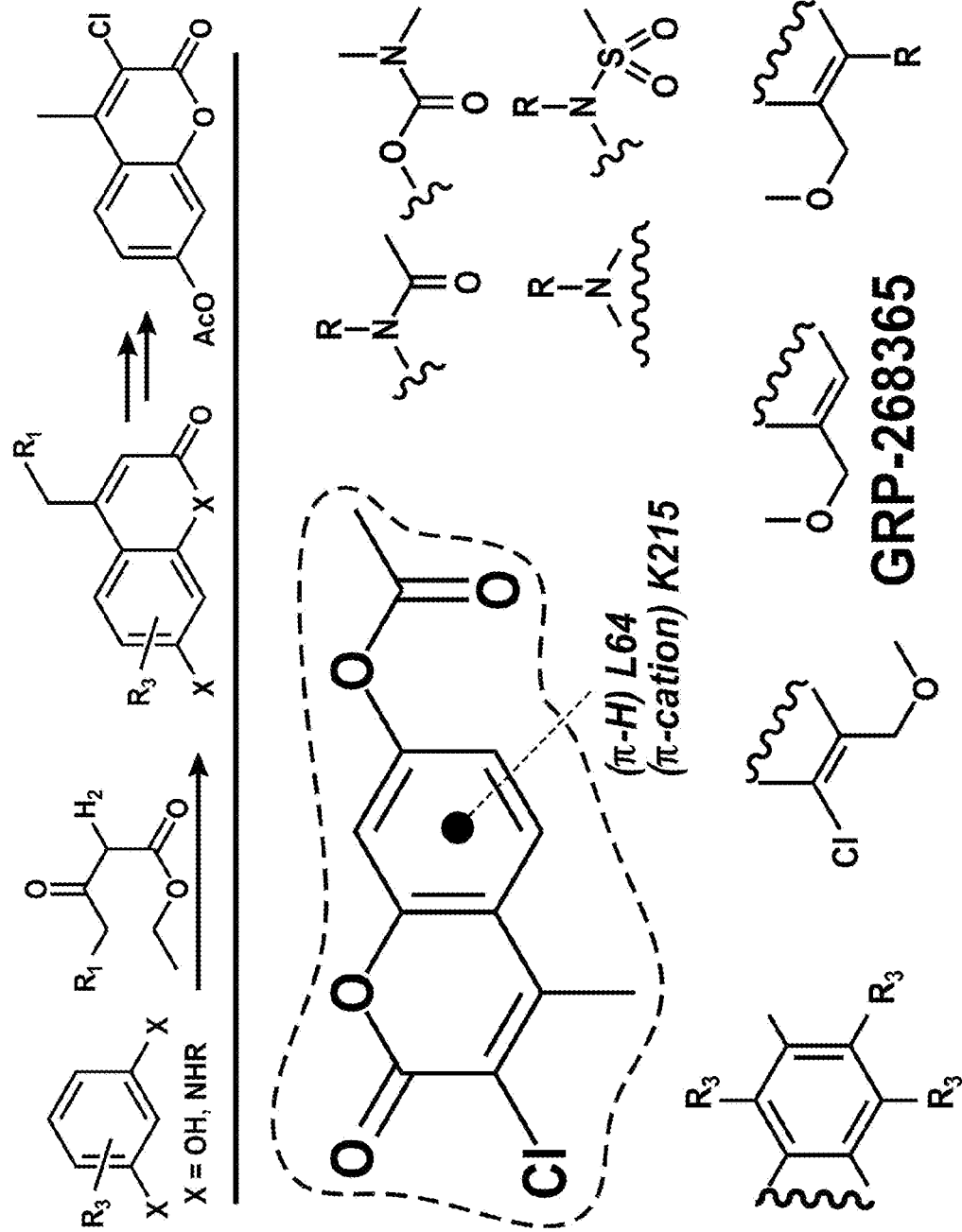
Figure 19:
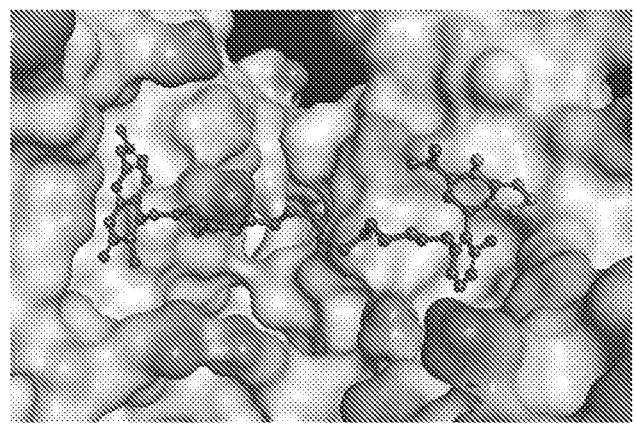
Figure 19:
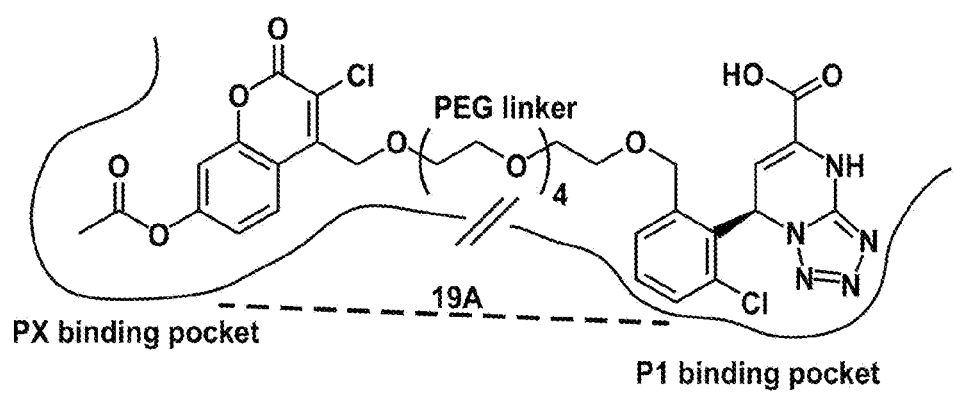
Figure 20:
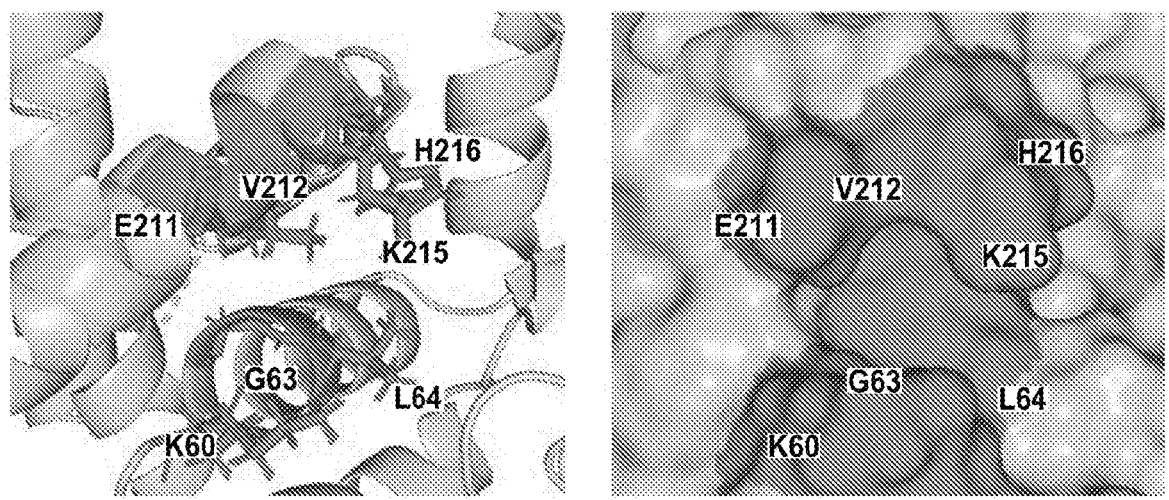

FIG. 16 shows predicted spatial distance between fragments docked into the discrete sites on adjacent protomers in the helical RSV genome assembly. The proximity of sites allows exploration of fragment linking independent of fragment growth to boost potency. Final linker design is SAR-driven, but short linkers (i.e. 5 PEG units) are predicted to favorably span the gap;

FIG. 17 shows a synthesis (top) and synthetic elaboration (bottom) schemes by example of a selected, confirmed fragment hit, GRP-171194using a racemic, multi-component approach to systematically substitute at the available phenyl group site, followed by manipulating the it-cloud with electron donating and withdrawing functionalities to probe both steric availability and stacking interactions. Similarly, both heterocycle manipulations and electron perturbing substitutions will probe the contribution of steric and it-stacking factors associated with the central bicycle 5 affinity. Isosteric substitutions will challenge the contribution of the carboxylate salt bridge. When activity data for these ligands are available, enantiomers of optimized compounds will be separated by chiral chromatography or resolution to probe the role of each enantiomeric configuration in activity. Enantio-specific synthetic methods will then be developed accordingly;

FIG. 18 shows the synthetic approach applied to the GRP-268365 scaffold. A priority will be installation of a more enzymatically stable replacement for the acetate ester with minimal affinity penalty. A second priority will be to assess steric constraints on substituents on the phenyl ring and the pyranone ring. First wave substitutions will include heteroalkyl moieties as pictured that will simultaneously explore the feasibility of attaching tethering groups in these positions. The available pilot NMR-derived docking poses suggest that substituted lactams in place of the lactone, for instance, will protrude into solvent space and be sterically feasible;

FIG. 19 shows preliminary molecular modeling which indicated that a 5-PEG linker is optimal (left) and a schematic of GRP-268365 and GRP-171194, showing the linker and link points (right); and FIG. 20 shows modeling representations of a newly identified druggable target site, designated Px, in the RSV N protein that is lined by residues Gly63, Leu64, Leu211, Val212, Lys215, and His216.

DETAILED DESCRIPTION

Terms

Before the present disclosure is described in greater detail, it is to be understood that this disclosure is not limited to embodiments described, and as such may, of course, vary. It is also to be understood that the terminology used herein is for the purpose of describing particular 30 embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any 10 publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

To the extent that any chemical formulas reported herein contain one or more chiral centers, the formulas are intended to encompass all stable stereoisomers, enantiomers, and diastereomers. It is also understood that formulas encompass all tautomeric forms.

It must be noted that, as used in the specification and the appended claims, the singular forms "a", "an", and "the" include plural referents unless the context clearly dictates otherwise.

"Subject" refers any animal, preferably a human patient, livestock, mouse model or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, "alkyl" means a noncyclic straight chain or branched, unsaturated or saturated hydrocarbon such as those containing from 1 to 20 carbon atoms. A "higher alkyl" refers to unsaturated or saturated hydrocarbon having 6 or more carbon atoms. A "$C_8$-$C_{18}$" refers to an alkyl containing 8 to 18 carbon atoms. Likewise a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, hexadecyl, dodecyl, tetradecyl, izosonyl, octadecyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3- methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like. Carbocyclyls include cycloalkyls and cycloalkenyls.

"Heterocarbocycles" or "heterocarbocyclyl" groups are carbocycles which contain from 1 to 4 heteroatoms independently selected from nitrogen, phosphorous, oxygen and sulphur which may be saturated or unsaturated (but not aromatic), monocyclic or polycyclic, and wherein the nitrogen and sulphur heteroatoms may be optionally oxidized (e.g. —S(O)—, —SO$_2$—, —N(O)—), and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

The terms "cycloalkyl" and "cycloalkenyl" refer to mono-, bi-, or tri homocyclic ring groups of 3 to 15 carbon atoms which are, respectively, fully saturated and partially unsaturated.

The term "substituted" refers to a molecule wherein at least one hydrogen atom is replaced with a substituent. When substituted, one or more of the groups are "substituents". The molecule may be multiply substituted. In the case of an oxo substituent (=O), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carb ocycloalkyl, heterocarb ocyclyl, heterocarbocycloalkyl, aryl, arylalkyl, heteroaryl, heteroarylalkyl.

The term "optionally substituted", as used herein, means that substitution is optional and therefore it is possible for the designated atom to be unsubstituted.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optionally has one or more, the same or different, substitutions. Derivatives may be prepared by any variety of synthetic methods or appropriate adaptations presented in synthetic or organic chemistry text books, such as those provided in "March's Advanced Organic Chemistry: Reactions, Mechanisms, and Structure", Wiley, 6th Edition (2007) Michael B. Smith or "Domino Reactions in Organic Synthesis", Wiley (2006) Lutz F. Tietze, hereby incorporated by reference.

Methods of use

In certain embodiments, the disclosure relates to methods of treating or preventing a viral infection comprising administering an effective amount of a compound of Formula A, Formula B, 10 Formula C or Formula E, or salts thereof disclosed herein to a subject in need thereof. In some embodiments, the subject is at risk of, exhibiting symptoms of, suffering from, or diagnosed with a viral infection such as RSV infections.

In some embodiments, the subject is at risk of, exhibiting symptoms of, or diagnosed with Respiratory syncytial virus (RSV), influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma- associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV); or is at risk of, exhibiting symptoms of, or diagnosed with RSV in addition to a co-infection with one of the above listed diseases.

In certain embodiments, methods disclosed herein are contemplated to be administered in combination with other the antiviral agent(s) such as abacavir, acyclovir, adefovir, amantadine, amprenavir, ampligen, arbidol, atazanavir, atripla, boceprevir, cidofovir, combivir, complera, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin , raltegravir, ribavirin, rimantadine, ritonavir, pyramidine, saquinavir, stavudine, stribild, tenofovir, tenofovir disoproxil, tenofovir alafenamide fumarate, tipranavir, trifluridine, trizivir, tromantadine, truvada, valaciclovir, valganciclovir, vicriviroc, vidarabine, viramidine, zalcitabine, zanamivir, or zidovudine, and combinations thereof. The methods of treatment and the pharmaceutical compounds of the present disclosure may also be administered with heretofore undisclosed antiviral agents acting of different components of RSV.

In certain embodiments, the disclosure contemplates the treatment or prevention of a viral infection using compounds disclosed herein, wherein viral infection is Respiratory syncytial virus (RSV).

In certain embodiments, the disclosure contemplates treatment or prevention of RSV infection by administering to a subject in need thereof, a composition comprising a compound that binds to P1 of RSV. In a method of treating or preventing RSV infection comprising administering a compound that binds to P1 of RSV, the compound can be a compound of Formula A, for example, GRP-171194, or variants of it as described herein.

In certain embodiments, the disclosure contemplates treatment or prevention of RSV infection by administering to a subject in need thereof, a composition comprising a compound that binds to Px (see FIG. 20). In a method of treating or preventing RSV infection comprising administering a compound that binds to Px of RSV, the compound can be a compound of Formula B, for example, GRP-268365, or variants of it as described herein.

In certain embodiments, the disclosure contemplates treatment or prevention of RSV infection by administering to a subject in need thereof, a composition comprising a compound that binds to both the P1 and the Px. In a method of treating or preventing RSV infection comprising administering a compound that binds to both P1 and Px of RSV, the compound can include a compound of Formula C, for example GRP-171194 and GRP-268365 linked with an appropriate linker.

In certain embodiments, the disclosure contemplates a method of identifying compounds useful in binding to the Px binding site in the RSV N protein that is lined by residues Gly63, Leu64, Leu211, Val212, Lys215, and His216, the method involving (i) providing a model comprising the druggable site, Px; (ii) providing one or more candidate inhibitor compounds potentially capable of targeting Px; (iii) evaluating contact between the candidate compounds and the residues in Px to determine which one of the candidate compounds have the ability to bind to 5 and/or fit into Px, and (iv) identifying the compounds, which based on this evaluation, have the ability to bind to and/or fit in the Px site and are potentially useful for inhibiting RSV infection. In the method of identifying compounds that bind Px, the model may comprise a region of the N protein that surrounds and supports the native structure of the Px pocket.

Formulations

The present disclosure includes pharmaceutical compositions comprising a compound of Formula A, Formula B, Formula C or Formula E) or salt thereof in combination with pharmaceutically acceptable excipients.

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

Pharmaceutical compositions for use in the present disclosure typically comprise an effective amount of a compound and a suitable pharmaceutically acceptable carrier. The preparations may be prepared in any manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778; 6,369,086; 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound of the present disclosure and at least one pharmaceutically acceptable carrier, diluent or excipient and/or adjuvant, and optionally one or more further pharmaceutically active compounds.

In certain embodiments, the pharmaceutical composition is in the form of a tablet, capsule, pill, gel, granules, aerosol, or aqueous buffer, such as a saline or phosphate buffer, or a nanoparticle formulation, emulsion, liposome, etc. The pharmaceutical preparations of the disclosure are preferably in a unit dosage form, and may be suitably packaged, for example in a box, blister, vial, 25 bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300, 400 or 500 mg per unit dosage.

The compounds can be administered by a variety of routes including the oral, ocular, rectal, transdermal, subcutaneous, intravenous, intramuscular or intranasal routes, depending mainly on the specific preparation used. In certain embodiments, the compound is administered by inhalation through the lungs.

The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, nanoparticles, aerosols and the like. Preferably, these formulations are employed in solid dosage forms suitable for simple, and preferably oral, administration of precise dosages. Solid dosage forms for oral administration include, but are not limited to, tablets, soft or hard gelatin or non- gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

In certain embodiments, the pharmaceutical composition comprises a compound disclosed herein and a propellant. In certain embodiments, an aerosolizing propellant is compressed air, ethanol, nitrogen, carbon dioxide, nitrous oxide, hydrofluoroalkanes (HFAs), 1,1,1,2, -tetrafluoroethane, 1,1, 1,2,3,3,3-heptafluoropropane or combinations thereof.

In certain embodiments, the disclosure contemplates a pressurized or unpressurized container comprising a compound herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers", are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as 5 benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulated for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and carbopol Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the Tradename tradename Eudragit®. In further preferred embodiments, the acrylic polymer comprises a mixture of two acrylic resin lacquers commercially available from Rohm Pharma under the Tradenames tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% :Eudragit® 90% RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and, capsules containing tablets, beads, or granules,. etc.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug- containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses is released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compound described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti- narcoleptics. "Adjunctive administration", as used herein, means the compound can be administered in the same dosage form or in separate dosage forms with one or more other active agents.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methyl salicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrab enozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

Examples

The present disclosure will now be described in more detail with reference to the following non-limiting examples. It should be noted that the particular assays used in the examples section are designed to provide an indication of activity. There are many other assays available to determine the activity of given compounds and a result in any one particular assay is therefore not determinative.

Fragment-based drug discovery and structure-activity relationship (SAR) by NMR can be applied to develop innovative inhibitors of the pneumovirus protein-ligand (P-L) interaction with RNP. Initial studies yielded two distinct anti-HPIV3 polymerase points-of-entry for hit-to-lead development and a promising starting point against RSV RNA-dependent RNA polymerase (RdRp) through target-hopping with the anti-MeV RdRp scaffold. To mitigate the risk of developmental failure of a singular hit scaffold, pilot studies were pursued in an innovative approach to identify 10 a second, structurally independent point-of-entry against the RSV polymerase target. It is hypothesized that the protein-protein-interaction (PPI) between RSV RdRp and the nucleocapsid (N) protein-encapsidated viral genome is highly druggable, albeit currently underexplored. Studies have shown that specific interactions between the pneumo- and paramyxovirus P-L polymerase complex and N:RNA genome are essential for virus replication.

Figure 7:
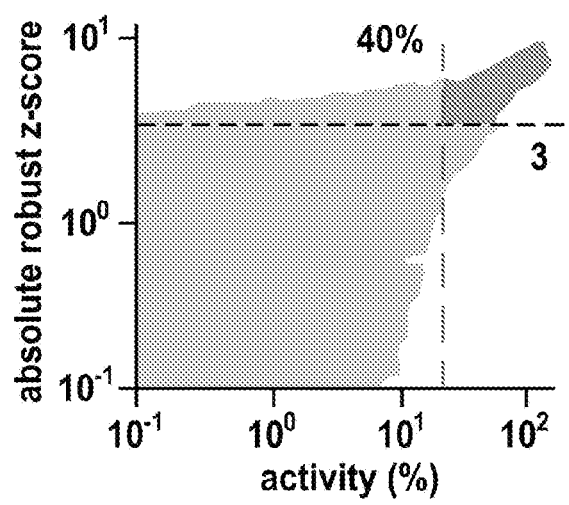
FIG. 7 shows a full library screen in 384-well format using purified RSV N and 11-mer 5-FAM-$P_{pep}$. Final compound concentration tested was 20 µM. Negative controls: purified N protein; 5-FAM- $P_{scpep}$. Normalized relative inhibition values and robust Z scores were used for hit identification.
Figure 8:
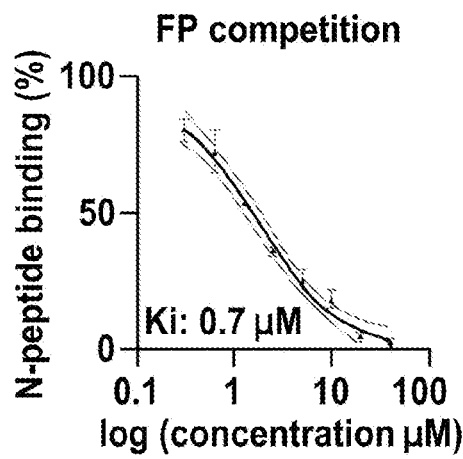
FIG. 8 is a FP assay with GRP-171194 (0.31-40 µM) which shows dose-dependent competition with 5-FAM-$P_{pep}$ (1 µM) for N. Regression curve (solid), 95% CI (dotted), Ki are shown.
Figure 9:
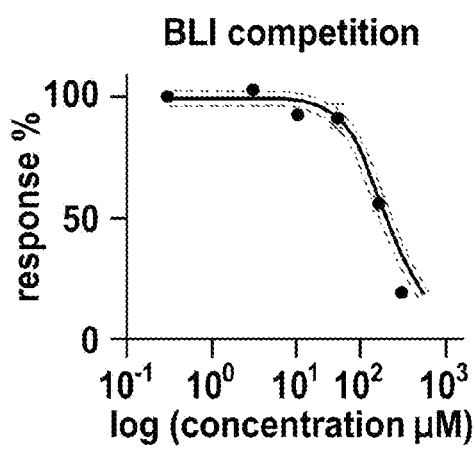
FIG. 9 shows a biolayer interferometry (BLI) competition assay for orthogonal counterscreen. Dissociation rates of purified N to P protein biosensors determined in presence of GRP-171194 under stringent conditions (PBS+BSA 0.01% +Tween20 0.002%). Dose-sensor response data plotted for each inhibitor concentration, showing dose-dependent inhibition.

While therapeutic targeting of PPIs is challenging, the biophysical properties of this interface are favorable for intervention: it is well mapped, a high-resolution crystal structure of the complex is available and the buried surface area and binding affinity ($K_D$=55 μM) are moderate. A biochemical FP assay was pioneered and validated to interrogate this PPI through targeted high throughput screening (HTS) (See FIGS. 1 to 6). Applied to a large-scale HTS campaign completed in pilot studies (FIG. 7), this protocol enables exploration of a broad chemical space including fragment libraries acquired for this present disclosure, which has a higher likelihood of PPI targeting but may require to hit-to-lead development.

Figure 13:
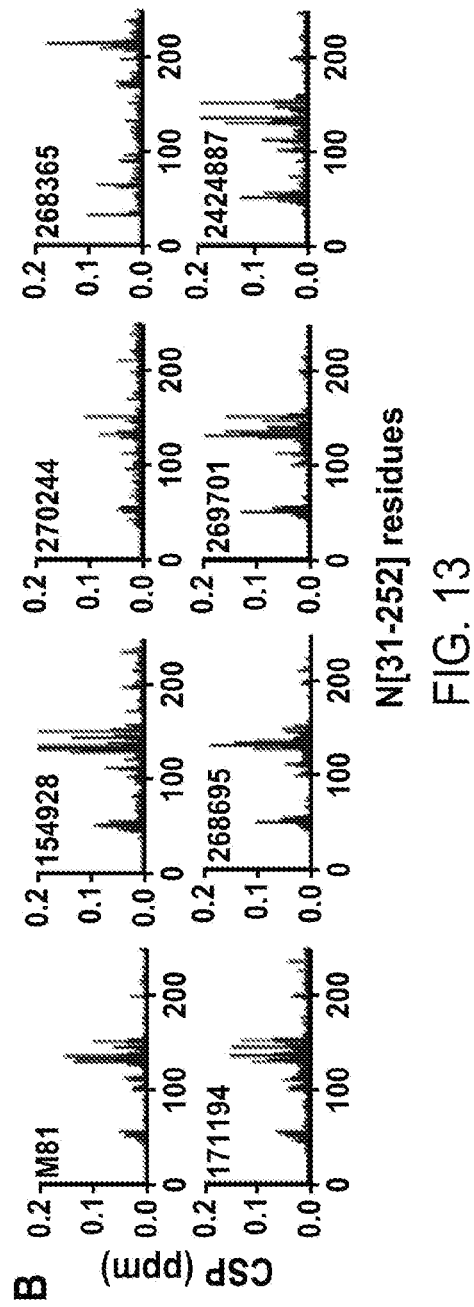
FIG. 13 is a $^1H^{15}$ N CSPs of 50 µ$N_{[31-252]}$ in the presence of 2-fold molar excess of 7 confirmed hit fragments at 295° K and analyzed with NMRFAM-SPARKY. Initial CSPs are >0.03 ppm, residues with shifts >2 SD are considered perturbed. Previously reported compound M81 was used as a control.

After direct counter-screening and in silico vetting of hit candidates using SwissADME and Lilly's reactivity & promiscuity filter set algorithms to identify lead potential and triage known assay PAINS, candidates were characterized in orthogonal biochemical counter-screens (FIGS. 7 to 11). A protein-observed NMR assay for RSV N and characterized docking poses of a subset of candidates was established through 41-amide chemical shift mapping (FIGS. 12 to 13).

HTS activities are achieved by exploring a small chemical warhead set (~1,590 entries) covering innovative covalent chemical space, characterizing docking poses of existing, confirming fragment hits, followed by synthetic development of lead candidate scaffolds suitable for cell-based potency testing, pharmacokinetic (PK) profiling, and PK-informed final synthetic optimization. Three distinct strategies: fragment growth, merger, and linking, can be simultaneously pursued.

Pilot Studies

Major HTS activities have ceased with successful completion of two full-scale campaigns in pilot studies. However, current open discovery and fragment based diversity sets were curated against covalently reactive compounds. The high density of lysine residues surrounding the binding pocket in the RSV N protein (FIG. 1) provides an attractive target for an innovative lysine-focused chemical warhead approach, broadening the chemical space explored. While lysine residues are typically underrepresented in protein interfaces, they are found enriched in critical interaction hotspots, actively contributing to complex formation. Parallel to the development of existing fragment hit candidates, a small Enamine set of 1,590 lysine-focused covalent fragments can be applied after integration into a screening collection to the validated array of primary assays and orthogonal screens (summarized in FIGS. 1 to 11). Substantiated by recent pilot achievements, the HTS capability to complete this exercise rapidly has been demonstrated. Hit candidates can be identified as detailed in FIGS. 7 to 11, and confirmed hits subjected to NMR- based characterization of the docking pose.

Characterization of Primary Ligand Docking Poses by Protein-Observed NMR:

Meaningful fragment-based drug discovery requires insight into the docking pose of confirmed hits. Due to the typically moderate initial fragment-to-target affinity, NMR spectroscopy is considered the gold-standard approach. The anti-RSV N-P PPI HTS campaign, and acquired resonance profiles of the RSV $N_{[31-252]}$ protein target in preparation of molecular docking based on chemical shift mapping (FIG. 12) has been completed. A >94% match of $^1H^{15}N$-heteronuclear single-quantum correlation (HSQC) spectra of RSV $N_{[31-252]}$ with reported experimental data (BioMagResBank ID 25705) was noted, establishing a solid assignment to the high-resolution RSV N crystal structures. Analysis of amide-bond chemical shift perturbations (CSPs) induced by the reported fragment hit M81 with NMRFAM-SPARKY returned matching CSP profiles (FIG. 13), confirming the validity of published data and successful assay set-up.

To assess a pilot docking pose, 7 of the confirmed fragment hits were generated and CSP profiles of RSV $N_{[31-252]}$ acquired with these compounds at different molar ratios. Profiles of 6 fragment hits were related to each other and the published hit M81, indicating engagement of residues surrounding the P1 binding pocket. By contrast, the seventh scaffold returned a unique profile, suggesting interaction with a discrete secondary site (FIG. 13) despite interference with N-P interaction in FP assays and biochemical counterscreens. Recognition of distinct binding sites by these hits was corroborated by BLI-based observation that interaction of the first 6 hits with $N_{[31-252]}$ was abolished by an R132E substitution in the P binding pocket, while the seventh hit was insensitive to this mutation. For an unbiased automated extraction of the docking pose, data can be processed using the SAMPLEX method. SAMPLEX-identified residues will serve as sites for molecular docking with the Molecular Operating Environment (MOE) package. MOEs 10 top-scoring poses can be rescored using one of the most advanced platforms for protein-ligand complex characterization by NMR, $^1H$ empirical chemical shift perturbation (HECSP) modeling combined with the NMRscore_P scoring function. To validate the approach, M81 was processed, for which a co-crystal structure with $N_{[31-252]}$ is available, and obtained a robust top scoring pose (complex RMSD 0.034Å) that maintained orientation and target interaction. To increase resolution for the most promising hits, $^{15}N$ HSQC-TOCSY profiles can be recorded, adding Ha and backbone chemical perturbations, and $^{15}N$-$^{13}C$ labeled target generated for triple resonance experiments (e.g. NH(CA-CO)HA).

Fragment Development:

Three independent strategies are available to develop lead candidates from fragment hits: i) fragment merger, combining ligands that discretely interrogate the same target site; ii) fragment growth, using the hit scaffold as anchor moiety; and iii) fragment linking, covalently tethering fragments that bind to discrete, but proximal sites.

Figure 14:
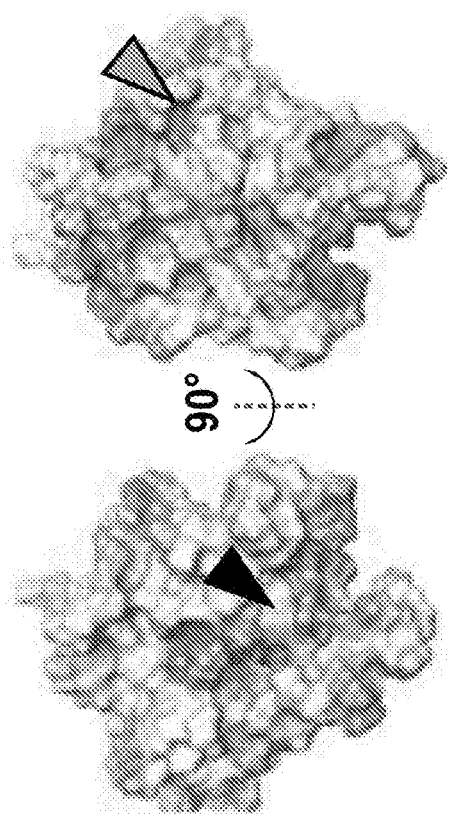

The SAMPLEX analysis pipeline has been applied to two selected fragments of a hit pool, one predicted to engage the P1 site and the other to dock into the Px site (FIGS. 14 to 15). All docking poses place GRP-268365 in a pocket on the distal surface of the N monomer, which is predicted to be surface exposed in the physiological genome assembly but can reasonably only impair N-P interface formation through a long-range steric effect. At project start, all data sets can be processed and docking poses synthetically challenged. The strategy for synthetic elaboration is exemplified in FIGS. 17 to 18. Top priorities are challenging the predicted τ-τ stacking interactions and importance of the carboxylate functionality of GRP-171194 and identifying stabilized alternatives to the metabolically labile ester functionality of GRP-268365. All analogs can be subjected to the FP assay to monitor interference with N-P interaction. Actives can be tested further in label-free BLI and through NMR chemical shift mapping The uncovering of a druggable second site in RSV N with long-range control over the N-P PPI opens an exciting path towards fragment linking, which has the potential to yield dramatic gains in potency. Examples of the linking of compounds that target P1 and Px include those of Formula C. The design of a bivalent compound simultaneously engaging both target sites on the same N protomer can take advantage of the fact that the pockets of adjacent N protomers in RSV genome assemblies are positioned within 18Å of each other (FIG. 16). In addition to generating avidity, engaging the pockets in neighboring N protomers alleviates concern that simultaneous docking into each site on the same monomer may be mutually exclusive, should binding to the secondary site trigger steric rearrangement of the N-P PPI. While SAR-refined docking poses inform final linker design and functionalization of each ligand, priority is given to linker length, steric hindrance, and entropic penalty of binding. Based on the current top scoring poses, for instance, a 5-PEG unit linker is predicted to satisfy spatial requirements but suffers from entropic penalty due to high flexibility. Using a flexible moiety as a starting point, rigidifying factors such as alkynes, their corresponding cis- or trans-double bonds, or heterocyclic groups can be introduced to lower entropic penalty and explore linker SAR. Linked fragments activity can be tested in the FP, BLI competition, and N-P pull down assays (FIGS. 7 to 11), all monitoring interaction of P with the 10-mer N ring assemblies rather than monomeric N.

Cell-based Antiviral Testing of Developmental Candidates:

Simultaneous to biochemical fragment hit characterization and development, anti-RSV potency can be quantified in cell-based assays. To overcome poor membrane permeability of carboxylate fragment hits, butyl and isopropyl esters expected to be cleaved intracellularly by endogenous esterases can be generated. Amide modifications and amino acid esters can also be explored with the goal to combine bioavailability with acceptable PK properties. Metabolic liabilities as in GRP-268365 can also be addressed synthetically.

For initial potency assessment, recombinant RSV reporter viruses can be employed to determine dose-response curves. These tests can be run routinely in an automated format, simultaneously assessing 8-fold serial compound dilutions in 3 independent replicates. Active concentrations can be calculated by four-parameter variable slope regression modeling. Individual prodrug candidates failing this assay can be tested for membrane permeability using a Caco-2 cell assay. Resistance-validated Caco-2 monolayers (TEER value >0.5×103Ω) will receive compound from the apical side, followed by LC-MS/MS-based quantification of substance intracellularly and in both chambers after 2-hour incubation. Atenolol, propranolol, and talinolol can be included as references and permeability coefficients (Papp) calculated. Candidates with poor Papp values can be reformulated synthetically. In parallel, all candidates can be subjected to rapid cytotoxicity screening, relying on PrestoBlue to monitor the redox potential of living cells after 48-hour exposure to a concentration range of compound. A validated automated cytotoxicity test pipeline has been established and can calculate $CC_{50}$ values through variable slope regression modeling.

With the anti-N-P HTS campaign largely completed and a diverse panel of confirmed fragment hits identified, covalent fragment screening, NMR-informed docking pose refinement and synthetic hit development can be undertaken. The combination of physical HTS dataset with experimental docking pose characterization and synthetic refinement can yield a panel of viable lead candidates for further development.

Exploration of the P1 pocket: Pro-drug Strategy

Having identified a key fragment that binds to the P1 pocket, the membrane impermeable carboxylate functional groups converted into the corresponding ester pro-drugs can assess the compounds in an in vitro assay against RSV. This conversion is a well-known strategy for overcoming membrane permeability issues associated with the charged carboxylate functionality (An Introduction to Medicinal Chemistry 5th Edition, Oxford University Press, p 259, 2013).

To this end, butyl and isobutyl esters of GRP-171194 should impart enough hydrophobicity to facilitate membrane permeation and should be readily cleaved in the cell by endogenous esterases. A range of esters with varying degrees of susceptibility towards esterases will be evaluated (some examples are shown below). If these are too proteolytically labile, a variety of related secondary and tertiary amides can be prepared to address this issue.

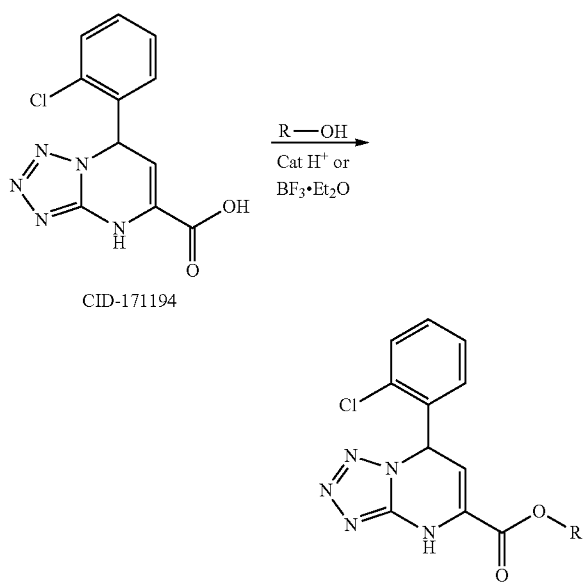

CID-171194

R = butyl
iso-butyl
tert-butyl
iso-propyl
benzyl
$-CH_2CF_3$

Analogs for SAR

Having assessed the efficacy of the ester pro-drug variants of GRP-171194, the SAR surrounding these scaffolds can be explored, guided by molecular modeling in combination NMR studies. The binding pose found by NMR for GRP-171194 can be confirmed and modification thereof can lead to a molecule that has tighter binding characteristics (increased interactions within the pocket)

The currently predicted binding pose in the P1 pocket can be confirmed by systematic substitution at various parts of GRP-171194, followed by NMR studies. In the currently predicted pose, shown below, the phenyl ring is buried within a tight hydrophobic pocket. Substitution at the 3- and 4-positions of the phenyl ring should be detrimental to the binding given that the small pocket will not be able to accommodate these substituents.

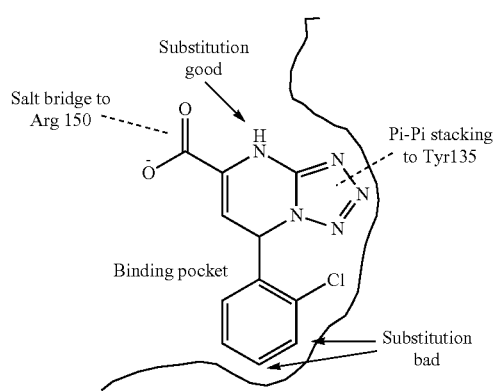 [SMILES: O=C(O)C1=CC(c2ccccc2Cl)n2nnnc2N1]

Synthesis of these derivatives should result in fragments which do not bind effectively, providing confirmation of the binding pose. Similarly, the pyrimidine ring —NH protrudes out of the pocket in the currently predicted binding pose and this should tolerate substitution without negatively affecting the binding.

Having confirmed the binding mode by NMR guided SAR, molecular modeling can be utilized to design compounds with improved interactions within the binding pocket, followed by their synthesis and confirmation by NMR studies. For example, Tyr135 is ideally positioned to form Pi-Pi stacking interactions with the core of the scaffold. Arg150 is located at the entrance to the pocket, near the carboxylate functionality. This provides a wonderful opportunity to optimize an electrostatic interaction.

In terms of accessing the variously substituted compounds, the scaffold of GRP-171194 can be synthesized via a multi-component coupling reaction between an aminotetrazole, a pyruvic acid derivative and an aldehyde derivative, as shown below. Variation of these three components allows easy access to numerous variously substituted derivatives, leading not only to tetrazole analogues, but also to triazole and imidazole analogues thereby also allowing for fine tuning of the polarity of the compounds (Synthetic Communications, 41:3635-3643, 2011). Separation of the enantiomers (at $R_a$) will be carried out by preparative chiral HPLC.

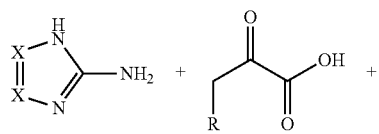

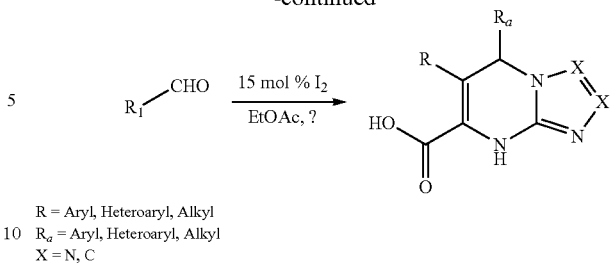

R = Aryl, Heteroaryl, Alkyl
$R_a$ = Aryl, Heteroaryl, Alkyl
X = N, C

Similarly, the SAR surrounding GRP-268365 will be explored, and the current binding hypothesis challenged. GRP-268365 and its derivatives can be synthesized from readily available resorcinol (Chemistry—A European Journal, 18:9901-9910, 2012). In addition, the analogous pyridinones will be prepared from O-protected hydroxyanilines to assess the importance of changing the pyran oxygen from an H-bond acceptor to an H-bond donor.

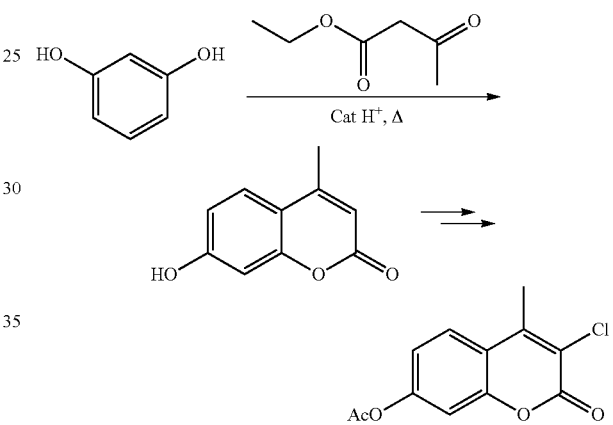

P1 Pocket and Adjacent Pocket Linker Strategy

Figure 1:
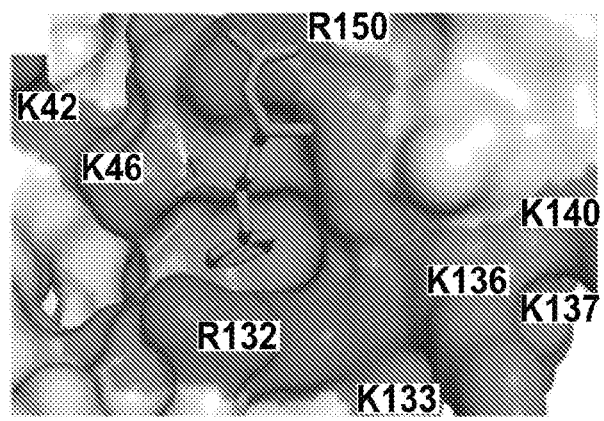
FIG. 1 shows a surface representation of RSV N showing target site P1 in complexed with C-terminal asp-phe residues of P.
Figure 2:
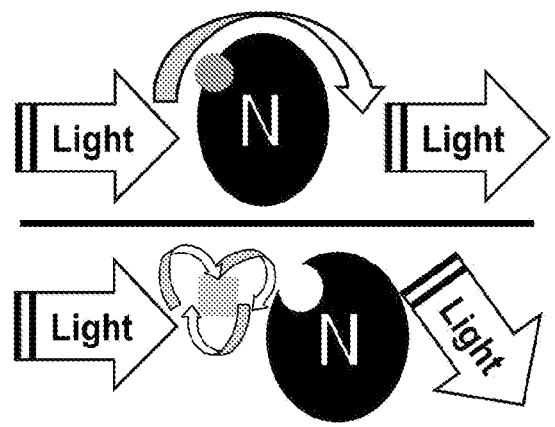
FIG. 2 illustrates the principle of FP interaction assay: excited by polarized light, a fluorophor-labeled small ligand (11-mer P peptide) emits largely depolarized light due to fast molecular rotation; binding a larger, slow rotating entity (purified N) reduces rotational movement, so emitted light is polarized.
Figure 3:
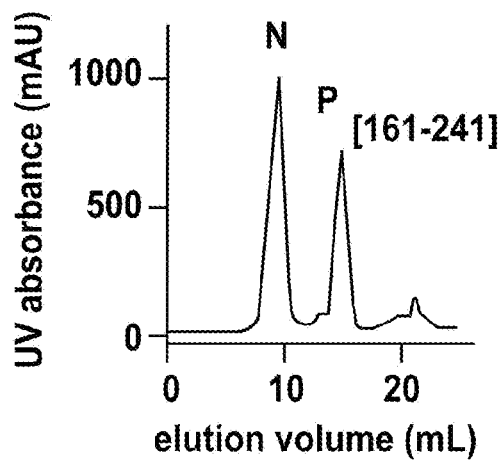
FIG. 3 is graph showing elution of purified recombinant N by size exclusion chromatography; N was co-expressed with dimeric P fragments for stabilization and proteolytic cleavage of P after affinity chromatography yields ~500 kDa 10-11-mer N ring assemblies.
Figure 4:
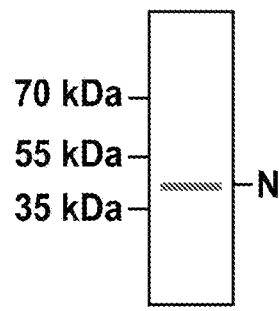
FIG. 4 shows authentication of N fraction by SDS-PAGE (500 ng purified input, Coomassie staining) and expected mobility pattern for monomeric N (43 kDa) is seen.
Figure 5:
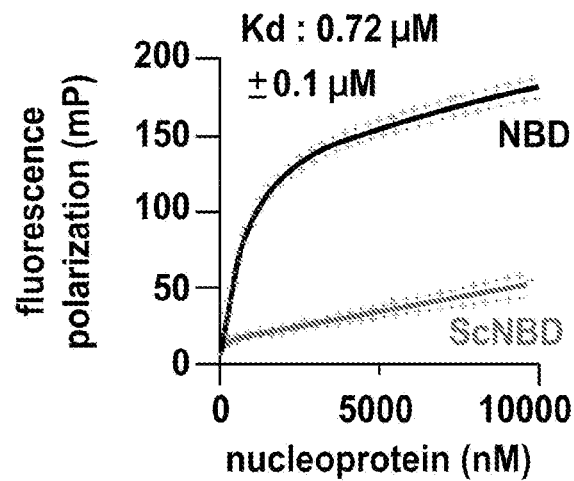
FIG. 5 shows FP assay development; 50 nM to 5 N titered vs. 1 µM 5-carboxyfluorescein-$P_{pep}$ (5-FAM-Ppep) or scrambled 5-FAM-$P_{scpep}$. $K_d$ values and 95% CI (dotted lines) shown.
Figure 6:
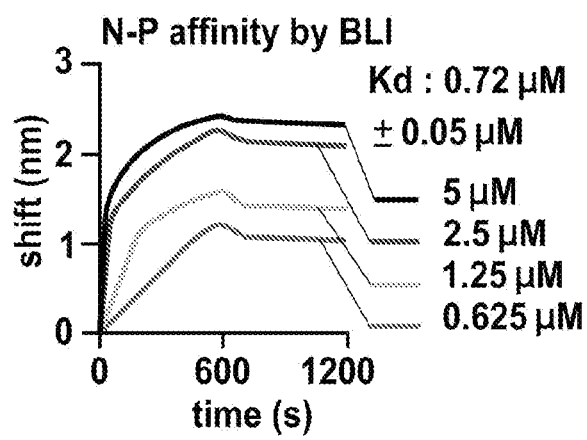
FIG. 6 shows assessment of purified N-P interaction by BLI; GST-tagged P immobilized on biosensors was incubated with soluble purified N (0.625-5µM); affinity ($K_d$±95% CI) calculated based on dissociation rates.

The discovery that GRP-268365 binds to a pocket adjacent to the P1 pocket, allows for a strategy of linking two fragments to facilitate simultaneous binding to the two pockets. Preliminary 25 modelling studies have indicated that a PEG linker chain consisting of 5-PEG units is optimal for linking the two fragments whilst retaining tight binding (FIG. 5—Left). The 5-PEG linker provides just enough length to span the region between the two binding pockets, without negatively affecting the binding pose of the two fragments within their respective pockets. A longer chain would have a higher entropic penalty of binding and therefore the minimum length to achieve the link without affecting the fragment binding is advantageous. The tether link points for GRP-171194 and GRP-268365 are shown in FIG. 19.

PEG ether linkages will lead to a flexible linker that is amenable to solvation, as would be required in this solvent accessible region between the two pockets. The introduction of rigidifying factors, such as alkynes or their corresponding cis- or trans-double bonds can be used to not only decrease the entropic penalty of binding, but also to develop a structure-activity relationship for the linker. Alternatively, the introduction of ester functionalities (which are also rigidifying factors) in various parts of the linker will lead to a hydrolysable linker group which can be cleaved by endogenous esterases, having first facilitated the simultaneous delivery of the tethered subunits, thereby allowing both fragments to bind to their respective binding sites without the linker, reducing the entropic penalty of binding (see below). Demonstration of this using our current fragment binders coupled to a first-generation linker would represent an important proof of concept. Of course, the ultimate viability of the hydrolyzable linker approach can only be truly assessed when more potent binding fragments are identified and coupled with a structurally optimized linker.

coupling of the linker. The installation of the more rigid alkyne containing linker can be accomplished in a similar manner, having previously prepared the required linker from the appropriate length PEG and propargyl bromide. The ester linkages can be implemented by initial reaction of the appropriate length PEG oligomer with maleic anhydride to form the terminal ester functionality. Conversion of the terminal PEG esters to the corresponding acid chlorides will set the stage for coupling of the appropriate 5 fragments to

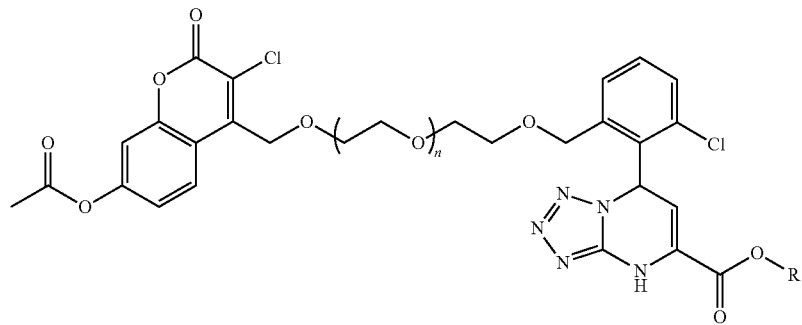

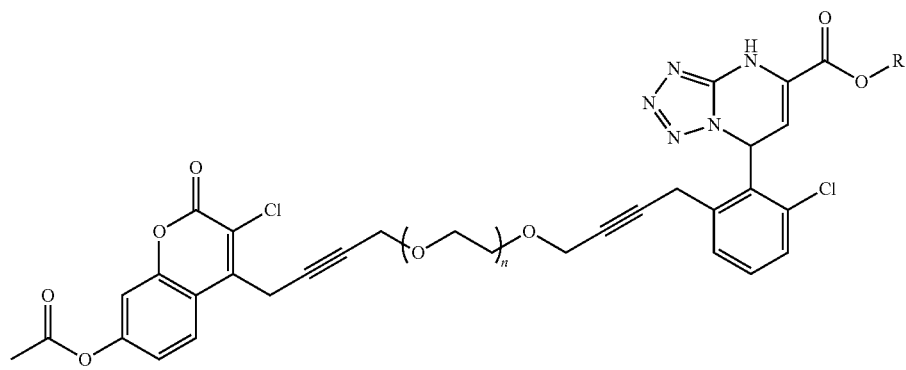

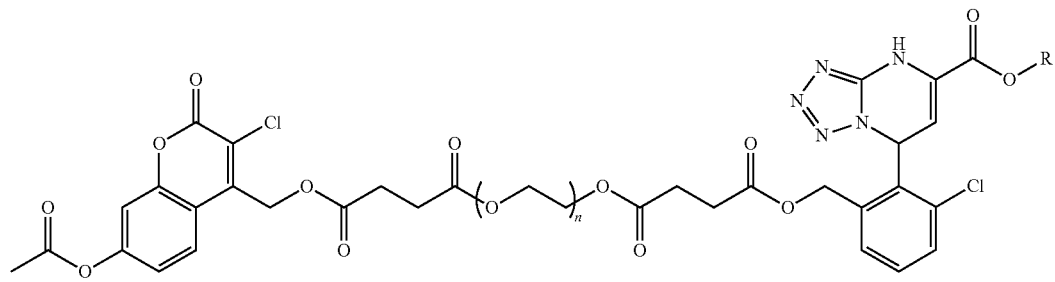

A range of variously sized and functionalized PEG oligomers are commercially available. In the case of the PEG ether linkages, we anticipate that the linker can be installed by $S_N2$ displacement of a benzylic halide, installed on the appropriate fragment. For example, synthesis of the benzyl chloride substituted version of GRP-171194 will allow for the linker. Importantly, since structural variants of both fragments can be easily prepared from readily available starting materials, additional tethering sites in each fragment could be evaluated to further optimize their binding pose efficiencies.

41 42
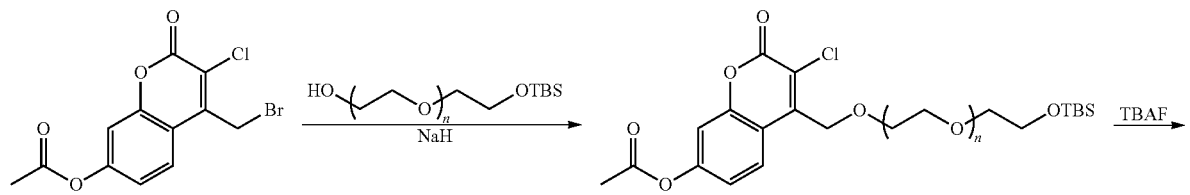
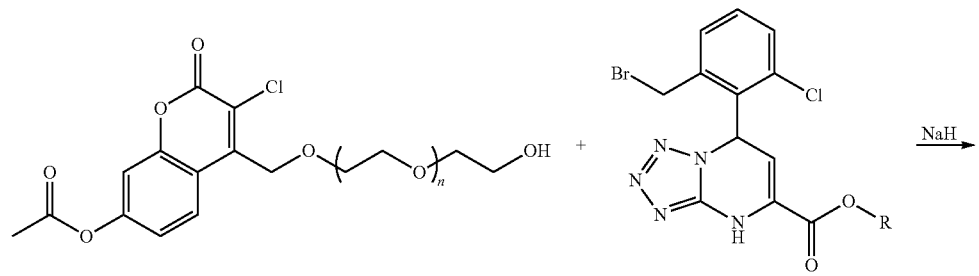
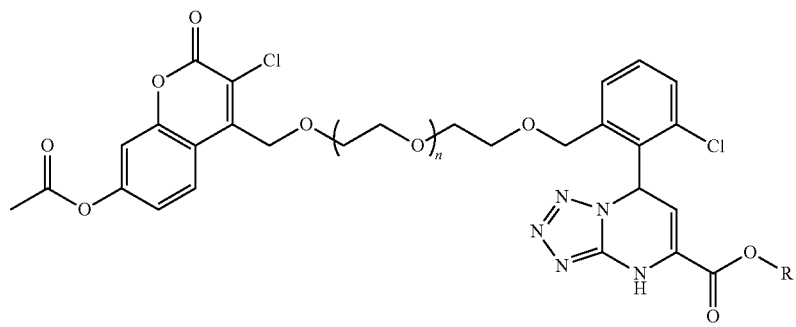
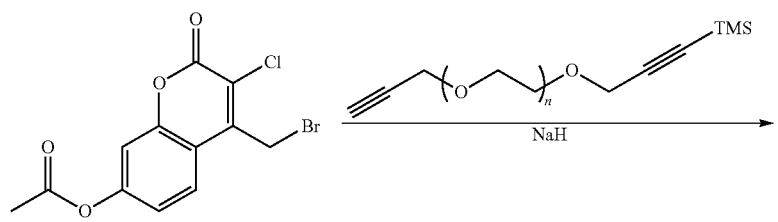
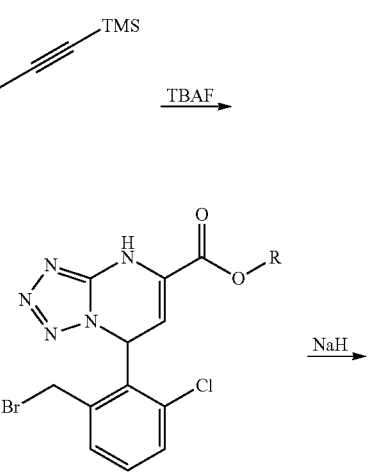

-continued

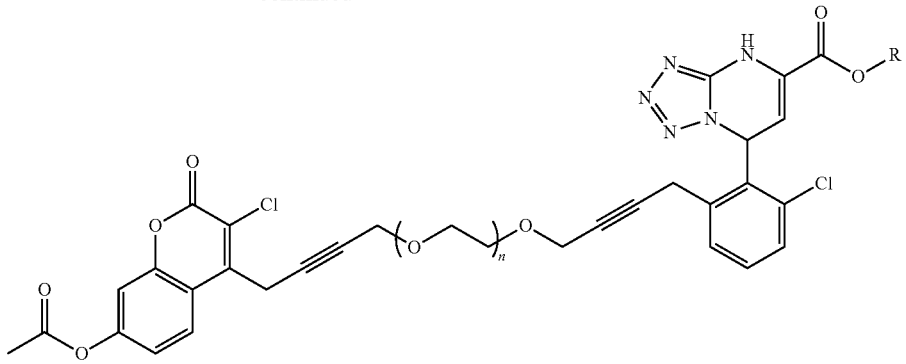

Synthetic Chemistry

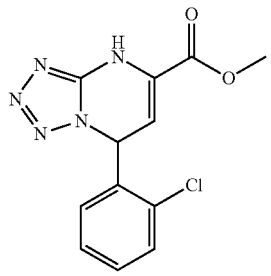

EJ3051: A 20mL vial equipped with a magnetic stir bar was charged with 70.0 mg of 7-(2-chlorophenyl)-4,7-dihydrotetrazolo[1,5-a]pyrimidine-5-carboxylic acid (0.250 mmol, 1 eq.), 9.24mg of DMAP (0,0800 mmol, 0.3eq.), 102 μL of methanol (2.52mmol, 10 eq.) and 1.5 mL of $CH_2Cl_2$. After addition of 58.0 mg of EDI (0.300 mmol, 1.2 eq.) and stirring at rt for 12 h, the reaction mixture was diluted with THF and water and the product was extracted with $CH_2Cl_2$ (3x) and dried over $Na_2SO_4$. The organics were concentrated and the crude product was recrystallized from a mixture of $CH_2Cl_2$/MeOH (3:1) affording 36 mg (49%) of the product as a white solid. $^1$H NMR (400 MHz, DMSO-$d_6$, ppm) δ: 10.81 (s, 1H), 7.53 (dd, J=7.3, 2.0 Hz, 1H), 7.45-7.37 (m, 2 H), 7.27 (dd, J=7.2, 2.1 Hz, 1H), 6.95 (d, J=3.7 Hz, 1H), 5.85 (d, J=3.7 Hz, 1H), 3.80 (s, 3H). $^{13}$C NMR (100 MHz, DMSO-$d_6$, ppm) δ: 161.30, 150.51, 135.58, 131.68, 130.81, 130.38, 130.04, 128.12, 127.67, 105.10, 56.99, 52.94. HRMS (ESI+) calcd for $C_{12}H_{11}O_2N_5Cl$([M+H]$^+$): 292.0596. Found: 292.0594, error −0.2 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=292.0 (M+H), 314.0 (M+Na), 605.0 (2 M+Na), t=0.736 min;

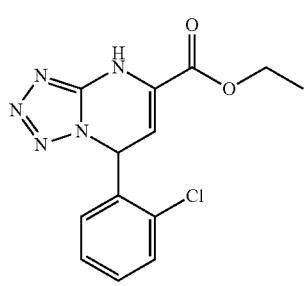 [SMILES: CCOC(=O)C1=CC(c2ccccc2Cl)n2nnnc2N1]

EJ3062: A 5 mL μW vial equipped with a magnetic stir bar was charged with 450 mg of 7-(2-chlorophenyl)-4,7-dihydrotetrazolo[1,5-a]pyrimidine-5-carboxylic acid (1.62 mmol, 1 eq.) and 173 μL of sulfuric acid (3.24 mmol, 2 eq.) dissolved in 2 mL of abs. EtOH. The reaction mixture was heated at 65° C. for 2 h and at 90° C. for 6 h. The reaction did not go to completion and more 600 pL of sulfuric acid (11.2 mmol, 6.9 eq.) dissolved in 1 mL of abs. EtOH was added and the reaction mixture was heated at 105° C. for 12 h. Then the mixture was cooled and poured in sat. $NaHCO_3$ solution, 3 mL of THF was added and the product was extracted with $CH_2Cl_2$ (3x) and dried over $Na_2SO_4$. The organics were concentrated affording 245 mg (49%) of the product as a white solid. $^1$H NMR (400 MHz, DMSO-$d_6$, ppm) δ: 10.79 (s, 1H), 7.53 (dd, J=7.3, 2.0 Hz, 1H), 7.46-7.37 (m, 2H), 7.28 (dd, J=7.2, 2.2 Hz, 1H), 6.95 (d, J=3.7 Hz, 1H), 5.84 (dd, J=3.8, 1.5 Hz, 1H), 4.32-4.19 (m, 2H), 1.26 (t, J=7.1 Hz, 3H). $^{13}$C NMR (100 MHz, DMSO-$d_6$, ppm) δ: 160.82, 150.55, 135.62, 131.71, 130.84, 130.41, 130.12, 128.15, 127.82, 104.93, 62.01, 57.03, 13.89. HRMS (ESI+) calcd for $C_{13}H_{13}O_2N_5Cl$ ([M+H]$^+$): 306.0752. Found: 306.0751, error −0.2 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=306.0 (M+H), 328.0 (M+Na), 611.0 (2M+H), 633.0 (2M+Na) t=0.907 min;

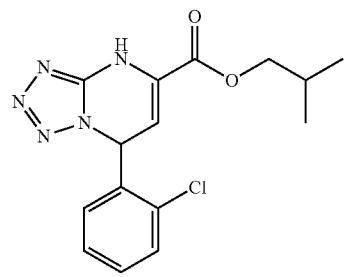

EJ3043: A 20mL vial equipped with magnetic stir bar was charged with 50.0 mg of 7-(2-chlorophenyl)-4,7-dihydrotetrazolo[1,5-a]pyrimidine-5-carboxylic acid (0.180 mmol, 1 eq.), 6.60 mg of DMAP (0,0540 mmol, 0.3 eq.), 166 μL of isobutanol (1.80 mmol, 10 eq.) and 1.5 mL of $CH_2Cl_2$. After addition of 41.4 mg of EDI (0.216 mmol, 1.2 eq.) and stirring at rt for 12 h, the reaction mixture was diluted with water and the product was extracted with $CH_2Cl_2$ (3x) and dried over $Na_2SO_4$. The organics were concentrated and the crude product was purified on silica gel column using 0 to 50% in CH₂Cl₂ as eluent affording 35 mg (58%) of the product as a white solid. ¹H NMR (400 MHz, CDCl₃, ppm) δ: 9.50 (s, 1H), 7.45 (dd, J=7.9, 1.4 Hz, 1H), 7.32 (dt, J=7.2, 1.8 Hz, OH), 7.27 (td, J=7.5, 1.5 Hz, 1H), 6.95 (dd, J=7.6, 1.8 Hz, 1H), 6.94 (d, J=3.7 Hz, 1H), 6.01 (dd, J=3.9, 1.7 Hz, 1H), 4.17 (A of ABX, $J_{AB}$=10.6 Hz, $J_{AX}$=6.9 Hz, 1H), 4.09 (B of ABX, $J_{AB}$=10.6 Hz, $J_{BX}$=6.8 Hz, 1H), 2.07 (nonet, J=6.7 Hz, 1H), 0.95 (d, J=6.7 Hz, 6H). ¹³C NMR (100 MHz, CDCl₃, ppm) δ: 160.98, 150.38, 135.36, 132.02, 130.45, 130.40, 128.59, 127.80, 127.48, 104.83, 72.66, 57.12, 27.60, 18.99, 18.96. HRMS (ESI+) calcd for $C_{15}H_{17}O_2N_5Cl$ ([M+H]⁺): 334.1065. Found: 334.1063, error −0.2 ppm. LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=333.8 (M+H), 355.9 (M+Na), 666.8 (2M+H), 689.8 (2M+Na) t=1.436 min;

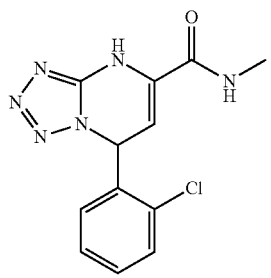

EJ3057: A 2 mL μW vial equipped with a magnetic stir bar and septum was charged with 70.0 mg of 7-(2-chlorophenyl)-4,7-dihydrotetrazolo[1,5-a]pyrimidine-5-carboxylic acid (0.250 mmol, 1 eq.) and 0.5 mL of DMF. Then 61.3 mg of CDI (0.380 mmol, 1.5 eq.) was added. After stirring at rt for 5 min, 34.0 mg of methylamine hydrochloride (0.500 mmol, 2 eq.) was added and the stirring was continued for 12 h. The reaction mixture was quenched by addition of water and the product was extracted with CH₂Cl₂ (3x) and dried over Na₂SO₄. The organics were concentrated and the crude product was purified on silica gel column (12 g) using 0 to 100% EA in CH₂Cl₂ as eluent affording 53 mg (72%) of the product as a beige solid. ¹H NMR (400 MHz, DMSO-d₆, ppm) δ: 10.41 (s, 1H), 8.45 (d, J=4.7 Hz, 1H), 7.57-7.49 (m, 1H), 7.47-7.35 (m, 2H), 7.25-7.18 (m, 1H), 6.91 (d, J=3.6 Hz, 1H), 5.60 (d, J=3.6 Hz, 1H), 2.68 (d, J=4.6 Hz, 3H). ¹³C NMR (100 MHz, DMSO-d₆, ppm) δ: 161.26, 150.59, 136.26, 131.55, 130.61, 130.51, 130.32, 129.74, 128.10, 98.86, 56.68, 26.06. HRMS (ESI+) calcd for $C_{12}H_{12}ON_6Cl$ ([M+H]⁺): 291.0756. Found: 291.0756, error −0.0 ppm. LC-MS (ESI-API, 254 nm) 75-95% MeOH in H₂O (0.1% HCO₂H), 3 min, 1.00 mL/min, C18(Agilent Zorbax XDB-18, 50 mm×4.6 mm, 3.5 μm), m/z=291.0 (M+H), 313.0 (M+Na), 581.0 (2M+H), 603.0 (2M+Na) t=0.599 min;

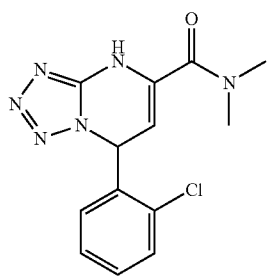 [SMILES: CN(C)C(=O)C1=CC(c2ccccc2Cl)n2nnnc2N1]

EJ3054: A 2 mL μW vial equipped with a magnetic stir bar and septum was charged with 70.0 mg of 7-(2-chlorophenyl)-4,7-dihydrotetrazolo[1,5-a]pyrimidine-5-carboxylic acid (0.250 mmol, 1 eq.) and 0.5 mL of DMF. Then 61.3 mg of CDI (0.380 mmol, 1.5 eq.) was added. After stirring at rt for 5 min, 41.1 mg of dimethylamine hydrochloride (0.500 mmol, 2 eq.) was added and the stirring was continued for 12 h. The reaction mixture was quenched by addition of water and the product was extracted with CH₂Cl₂ (3x) and dried over Na₂SO₄. The organics were concentrated and the crude product was purified on silica gel column (12 g) using 0 to 100% EA in CH₂Cl₂ as eluent affording 47 mg (61%) of the product as a beige solid. ¹H NMR (400 MHz, DMSO-d₆, ppm) δ: 10.71 (s, 1H), 7.54-7.49 (m, 1H), 7.43-7.38 (m, 2H), 7.31- 7.27 (m, 1H), 6.86 (d, J=3.4 Hz, 1H), 5.02 (d, J=3.4 Hz, 1H), 3.05 (s, 3H), 2.89 (s, 3H). ¹³C NMR (100 MHz, DMSO-d₆, ppm) δ: 163.51, 150.14, 136.33, 131.65, 131.22, 130.58, 130.35, 129.93, 128.06, 97.12, 56.96, 38.20, 34.59. HRMS (ESI+) calcd for $C_{13}H_{14}ON_6Cl$([M+H]⁺): 305.0912. Found: 305.0910, error −0.2 ppm. LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=305.0 (M+H), 327.0 (M+Na), 609.2 (2M+H), 631.0 (2M+Na) t=0.604 min;

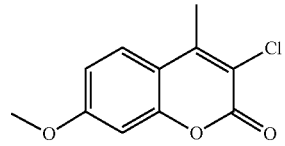

EJ3061: A 2 mL μW vial equipped with a magnetic stir bar and septum was charged with 120 mg of 3-chloro-7-hydroxy-4-methyl-2H-chromen-2-one (0.570 mmol, 1 eq.), 158 mg of K₂CO₃ (1.14 mmol, 2 eq.) and 1 mL of acetone. After heating at 65° C. for 30 min, 36.0 μL of methyl iodide (0.570 mmol, 1 eq.) was added. After stirring at 65° C. 6h, the reaction mixture was quenched by addition of water and the product was extracted with CH₂Cl₂ (3x) and dried over Na₂SO₄. The crude product was re-dissolved in EA, washed with sat. NaHCO₃ solution and dried over Na₂SO₄. The organics were concentrated and the crude product was purified by recrystallization from abs. EtOH affording 68mg (53%) of the product as a white solid. ¹H NMR (400 MHz, CDCl₃, ppm) δ: 7.49 (d, J=8.9 Hz, 1H), 6.88 (dd, J=8.9, 2.6 Hz, 1H), 6.76 (d, J=2.6 Hz, 1H), 3.86 (s, 3H), 2.52 (s, 3H). ¹³C NMR (100 MHz, CDCl₃, ppm) δ: 162.44, 157.31, 152.96, 147.95, 125.81, 117.58, 113.11, 112.83, 100.63, 55.76, 16.11. HRMS (ESI+) calcd for $C_{11}H_{10}O_3Cl$ ([M+H]⁺): 225.0313. Found: 225.0312, error −0.1 ppm. LC-MS (ESI-API, 210 nm) 75-95% MeOH in H₂O (0.1% HCO₂H), 3 min, 1.00 mL/min, C18 (Agilent Zorbax XDB-18, 50 mm×4.6 mm, 3.5 μm), m/z=225.0 (M+H), 247.0 (M+Na), 471.0 (2M+Na) t=1.011 min; (negative absorption at 245 nm)

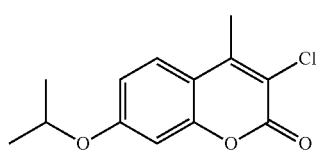 [SMILES: Cc1c(Cl)c(=O)oc2cc(OC(C)C)ccc12]

EJ3063: A 2 mL μLW vial equipped with a magnetic stir bar and septum was charged with 120 mg of 3-chloro-7-hydroxy-4-methyl-2H-chromen-2-one (0.570 mmol, 1 eq.), 158 mg of K$_2$CO$_3$ (1.14 mmol, 2 eq.) and 1 mL of acetone. After heating at 65° C. for 30 min, 114 μL of 2-iodopropane (1.14 mmol, 2 eq.) was added. After stirring at 65° C. for 6h, the reaction did not go to completion. More 684 μEL of 2-iodopropane (6.84 mmol, 12 eq.) was added and the mixture was stirred at rt for 12 h and at 75° C. for 18 h. Then the reaction mixture was quenched by addition of water and the product was extracted with CH$_2$Cl$_2$ (3x), washed with sat. NaHCO$^3$ solution and dried over Na$_2$SO$_4$. The organics were concentrated and the crude product was purified by recrystallization from abs. EtOH affording 36 mg (25%) of the product as a white solid. $^1$H NMR (400 MHz, CDCl$^3$, ppm) δ: 7.50 (d, J=8.9 Hz, 1H), 6.86 (dd, J=8.9, 2.5 Hz, 1H), 6.79 (d, J=2.5 Hz, 1H), 4.61 (hept, J=6.1 Hz, 1H), 2.54 (s, 3H), 1.37 (d, J=6.0 Hz, 6H). $^{13}$C NMR (100 MHz, CDCl$_3$, ppm) δ: 160.93, 157.51, 153.10, 148.02, 125.85, 117.43, 114.08, 112.88, 102.06, 70.75, 21.73, 16.13. HRMS (ESI+) calcd for C$_{13}$H$_{14}$O$_3$Cl ([M+H]$^+$): 253.0626. Found: 253.0625, error −0.1 ppm. LC-MS (ESI-API, 210 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=253.0 (M+H), 275.0 (M+Na), 527.0 (2M+Na) t=1.616 min; (negative absorption at 245 nm)

mmol) in anhydrous DMF (1 mL). The white solid EDCI (76.63 mg, 0.4000 mmol) was added, and the mixture dissolved and turned yellow; then DMAP (16.28 mg, 0.1300 mmol) was added, and the color turned dark. Lastly, 2,2,2-trifluoroethanol (0.19mL, 2.67mmol) (dried over activated 4 Å molecular sieves) was dropwise added, and the reaction stirred at ambient temperature for two days with monitoring by TLC. Reaction was quenched by addition of saturated ammonium chloride solution before the product was extracted with ethyl acetate and washed with brine solution. The organic extract was dried over sodium sulfate, filtered and concentrated to an orange residue which was purified via silica gel flash column chromatography using a gradient of 0-35% ethyl acetate in DCM to afford the desired compound (39.8 mg, 41.5% yield). $^1$H NMR (500MHz, d6-DMSO, ppm) δ: 10.88 (s, 1H), 7.42 (dd, J=7.7, 1.6 Hz, 1H),7.33 (td, J=7.6, 1.9 Hz, 1H), 7.29 (td, J=7.5, 1.6 Hz, 1H), 7.09 (dd, J=7.5, 1.7 Hz, 1H), 6.90 (d, J=3.8 Hz, 1H), 5.92 (dd, J =3.8, 1.7 Hz, 1H), 4.83-4.75 (m, 1H), 4.73-4.65 (m, 1H). $^{13}$C NMR (125 MHz, d6-DMSO, ppm) δ: 159.2, 150.1, 135.0, 131.5, 130.2, 129.9, 129.0, 127.5, 126.6, 122.3 (q, $^1J_{CF}$=275 Hz), 105.9, 60.7 (q, $^2J_{CF}$=36 Hz), 56.5. $^{19}$F NMR (282 MHz, d6-DMSO, ppm) δ: −72.87 (t, J=8.6 Hz). HRMS (ESI+) m/z: [M+H]$^+$ calcd for C$_{13}$H$_{10}$ClF$_3$N$_5$O$_2$ 360.04696, found 360.04687.

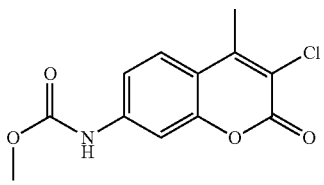 [SMILES: COC(=O)Nc1ccc2c(C)c(Cl)c(=O)oc2c1]

EJ3066: The compound was prepared according to a method provided in *Bioorg. Med. Chem. Lett.*2015, 25, pp. 508-513. $^1$H NMR (400 MHz, DMSO-d$_6$, ppm) δ: 10.26 (s, 1H), 7.80 (d, J=8.8 Hz, 1H), 7.59 (d, J=2.1 Hz, 1H), 7.44 (dd, J=8.8, 2.2 Hz, 1H), 3.72 (s, 3H), 2.53 (s, 3H). $^{13}$C NMR (100 MHz, DMSO-d$_6$, ppm) δ: 156.41, 153.78, 151.80, 148.66, 142.85, 126.61, 116.94, 114.73, 113.96, 104.18, 52.14, 16.01. HRMS (ESI+) calcd for C$_{12}$H$_{11}$O$_4$NCl ([M+H]$^+$): 268.0371. Found: 268.0372, error 0.1 ppm. LC-MS (ESI-API, 210 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=557.0 (2M+Na), 268.0 (M+H), 290.0 (M+Na), t=0.863 min; (negative absorption at 254 nm)

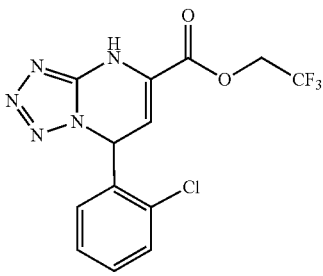 [SMILES: O=C(OCC(F)(F)F)C1=CC(c2ccccc2Cl)n2nnnc2N1]

ZD-3-064: In an oven-dried 10-mL Schlenck tube with stir bar was suspended 7-(2-chlorophenyl)-4,7-dihydrotetrazolo[1,5-a]pyrimidine-5-carboxylic acid (74 mg, 0.2700

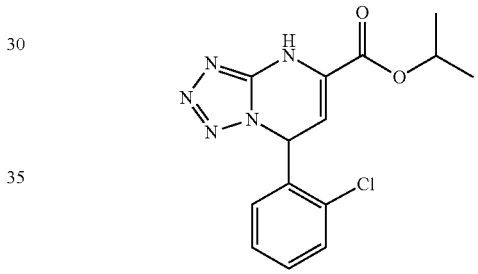

ZD-3-069: In a 20-mL scintillation vial with stir bar were dissolved 7-(2-chlorophenyl) -4,7-dihydrotetrazolo[1,5-a]pyrimidine-5-carboxylic acid (146 mg, 0.53 mmol) and triphenylphosphine (165.49 mg, 0.63 mmol) in anhydrous THF (2.5 mL) to give a colorless solution. Isopropyl alcohol (44.28 μL, 0.58 mmol) was added, and the solution was chilled to 0° C. before diisopropyl azodicarboxylate (122.68 μL, 0.63 mmol) was dropwise added with stirring to give a yellow solution. The ice bath was removed, and the reaction stirred at ambient temperature for an hour before being concentrated; the residue was purified via silica gel flash column chromatography with a 0-50% gradient of ethyl acetate in hexanes. The product mixture was then triturated with water to afford the desired compound as a white solid (0.13 g, 77% yield). $^1$H NMR (500 MHz, d6-DMSO, ppm) δ: 10.74 (s, 1H), 7.53 (dd, J=7.7, 1.5 Hz, 1H), 7.45-7.38 (m, 2H), 7.27 (dd, J=7.4, 1.5 Hz, 1H), 6.95 (d, J=3.7 Hz, 1H), 5.81 (dd, J=3.7, 1.5 Hz, 1H), 5.06 (hept, J=6.1 Hz, 1H), 1.26 (t, J=6.2 Hz, 6H). $^{13}$C NMR (125 MHz, d6-DMSO, ppm) δ: 160.3, 150.6, 135.6, 131.7, 130.8, 130.4, 130.1, 128.13, 128.05, 104.7, 70.0, 57.0, 21.4 (x2). HRMS (ESI+) m/z: [M+H]$^+$ calcd for C$_{14}$H$_{15}$ClN$_5$O$_2$ 320.09088, found 320.09091.

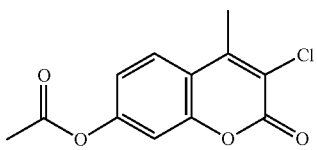 [SMILES: CC(=O)Oc1ccc2c(C)c(Cl)c(=O)oc2c1]

ZD-3-066: In a 2-mL ▢W vial with stir bar were combined 3-chloro-7-hydroxy-4-methyl-chromen-2-one (200 mg, 0.95 mmol), acetic anhydride (1 mL), and catalytic DMAP (11.6 mg, 0.09 mmol) to give a white suspension. The reaction stirred at ambient temperature for 3 hours before being quenched by saturated sodium bicarbonate solution. The product was extracted with ethyl acetate and washed with brine solution before the organic layer was collected, dried over sodium sulfate, filtered and concentrated to afford the desired product as a white solid (238mg, 99% yield). $^1$H NMR (600 MHz, CDCl$_3$, ppm) δ: 7.64 (d, J=8.7 Hz, 1H), 7.15 (d, J=2.1 Hz, 1H), 7.13 (dd, J=8.7, 2.3 Hz, 1H), 2.59 (s, 3H), 2.34 (s, 3H). $^{13}$C NMR (150 MHz, CDCl$_3$, ppm) δ: 168.8, 156.9, 153.0, 152.1, 147.4, 125.8, 120.7, 118.9, 117.7, 110.6, 21.3, 16.4. HRMS (APCI+) m/z: [M+H]$^{30}$ calcd for C$_{12}$H$_{10}$ClO$_4$ 253.02621, found 253.02660.

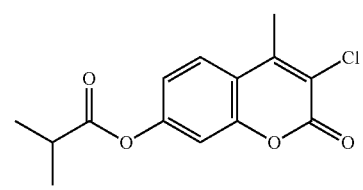 [SMILES: Cc1c(Cl)c(=O)oc2cc(OC(=O)C(C)C)ccc12]

ZD-3-067: In an oven-dried 10-mL Schlenck tube with stir bar was dissolved 3-chloro-7-hydroxy-4-methyl-chromen-2-one (200 mg, 0.95 mmol) in anhydrous DCM (3.5 mL). The white solid EDCI (273.06 mg, 1.42 mmol) was added, turning the solution yellow; DMAP (11.6 mg, 0.09 mmol) was added, and the color turned dark. Lastly, 2-methylpropanoic acid (0.11mL, 1.19 mmol) was dropwise added, and the reaction stirred at ambient temperature overnight. The reaction was quenched with water, and the product was extracted with DCM; the organic layer was collected, dried over sodium sulfate, filtered and concentrated. The residue was purified via silica gel flash column chromatography using a gradient of 0-50% ethyl acetate in hexanes to afford the product as a white solid (0.232 g, 87% yield). $^1$H NMR (600 MHz, CDCl$_3$, ppm) δ: 7.63 (d, J=8.7 Hz, 1H), 7.13 (d, J=2.2 Hz, 1H), 7.11 (dd, J=8.7, 2.3 Hz, 1H), 2.87-2.80 (m, 1H), 2.59 (s, 3H), 1.33 (d, J=7.0 Hz, 6H). $^{13}$C NMR (150 MHz, CDCl$_3$, ppm) δ: 175.0, 156.9, 153.4, 152.1, 147.4, 125.8, 120.6, 118.9, 117.6, 110.5, 34.3, 19.0 (x2), 16.4. HRMS (ESI+) m/z: [M+H]$^+$ calcd for C$_{14}$H$_{14}$ClO$_4$ 281.05751, found 281.05745.

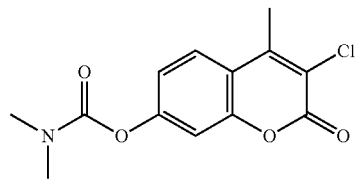 [SMILES: Cc1c(Cl)c(=O)oc2cc(OC(=O)N(C)C)ccc12]

ZD-3-070: In a 20-mL scintillation vial with stir bar was dissolved 3-chloro-7-hydroxy-4-methyl-chromen-2-one (152mg, 0.72 mmol) in anhydrous DMF (2 mL) to give a light yellow-brown solution; cesium carbonate (306 mg, 0.94 mmol) was added, turning the reaction a vibrant yellow. Lastly, dimethylcarbamoyl chloride (86 uL, 0.94 mmol) was added with stirring, releasing a vapor. The reaction was sealed and the yellow solution turned brown as a precipitate formed. After 3 hours of stirring at ambient temperature the reaction was diluted with ethyl acetate and quenched by addition of 5% aqueous citric acid solution, producing a white precipitate which dissolved upon dilution with brine solution. The yellow product was extracted with ethyl acetate and twice washed with brine solution; the organic extract was dried over sodium sulfate, filtered and concentrated to a yellow solid. Purification via silica gel flash column chromatography with a gradient of 0-80% ethyl acetate in hexanes afforded the desired product as a white solid (154 mg, 76% yield). $^1$H NMR (400 MHz, CDCl$_3$, ppm) δ: 7.62-7.58 (m, 1H), 7.17-7.14 (m, 2H), 3.12 (s, 3H), 3.03 (s, 3H), 2.58 (s, 3H). $^{13}$C NMR (125 MHz, CDCl$_3$, ppm) δ: 157.0, 154.1, 153.8, 152.1, 147.5, 125.6, 120.2, 119.0, 117.1, 110.4, 37.0, 36.7, 16.4. HRMS (ESI+) m/z: [M+H]$^+$ calcd for C$_{13}$H$_{13}$ClNO$_4$ 282.05276, found 282.05355.

| Name | Structure | $K_i$ in FP (μM) | IC$_{50}$ HEp2 cells RSV (μM) | CC$_{50}$ HEp2 cells RSV (μM) | IC$_{50}$ BEAS2B cells RSV (μM) | CC$_{50}$ BEAS2B cells RSV (μM) |
|---|---|---|---|---|---|---|
| GRP-268365 | 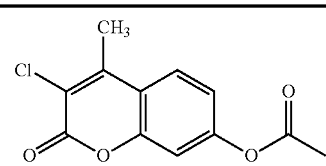 | 2.2 | nd | nd | nd | nd |
| ZD-3-067 | 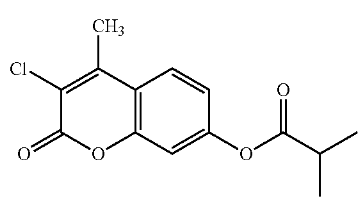 [SMILES: Cc1c(Cl)c(=O)oc2cc(OC(=O)C(C)C)ccc12] | 1.6 | 6.5 | 7 | 136 | 251 |

-continued

| Name | Structure | $K_i$ in FP (μM) | $IC_{50}$ HEp2 cells RSV (μM) | $CC_{50}$ HEp2 cells RSV (μM) | $IC_{50}$ BEAS2B cells RSV (μM) | $CC_{50}$ BEAS2B cells RSV (μM) |
|---|---|---|---|---|---|---|
| EJ21257 | 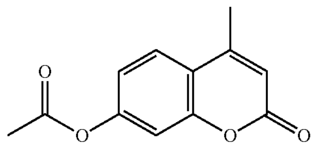 [SMILES: CC(=O)Oc1ccc2c(C)cc(=O)oc2c1] | 2.9 | >300 | >100 | >300 | 113 |
| EJ3066 | 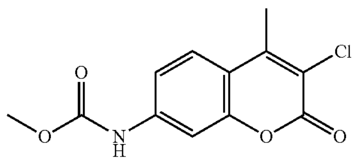 [SMILES: COC(=O)Nc1ccc2c(C)c(Cl)c(=O)oc2c1] | >300 | >100 | >100 | 129.6 | >100 |
| EJ3063 | 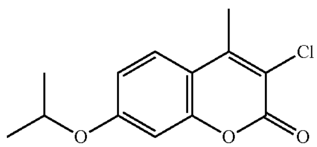 [SMILES: Cc1c(Cl)c(=O)oc2cc(OC(C)C)ccc12] | >300 | 1.9 | 1.2 | 14.6 | >300 |
| EJ3061 | 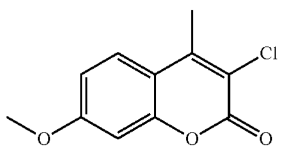 | >300 | nd | nd | nd | nd |
| AX801 | 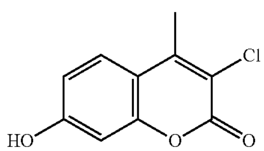 | >300 | nd | nd | 65 | 116 |
| GRP-171194 | 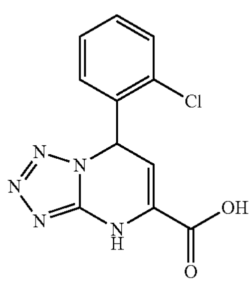 [SMILES: O=C(O)C1=CC(c2ccccc2Cl)n2nnnc2N1] | 2.4 | >300 | >300 | >300 | >300 |
| RJW-3-024 | 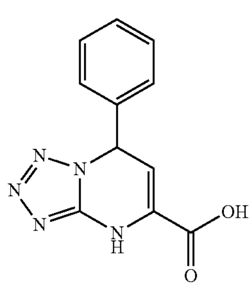 [SMILES: O=C(O)C1=CC(c2ccccc2)n2nnnc2N1] | 10 | nd | nd | >300 | >300 |

-continued

| Name | Structure | $K_i$ in FP (µM) | $IC_{50}$ HEp2 cells RSV (µM) | $CC_{50}$ HEp2 cells RSV (µM) | $IC_{50}$ BEAS2B cells RSV (µM) | $CC_{50}$ BEAS2B cells RSV (µM) |
|---|---|---|---|---|---|---|
| ZD-3-069 | 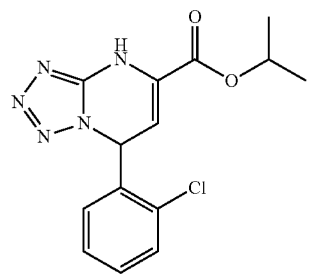 [SMILES: CC(C)OC(=O)C1=CC(c2ccccc2Cl)n2nnnc2N1] | >300 | >300 | >300 | >300 | >300 |
| ZD-3-064 | 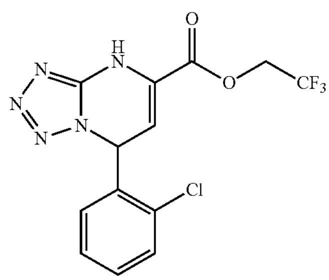 [SMILES: O=C(OCC(F)(F)F)C1=CC(c2ccccc2Cl)n2nnnc2N1] | >300 | nd | nd | >300 | >300 |
| EJ3062 | 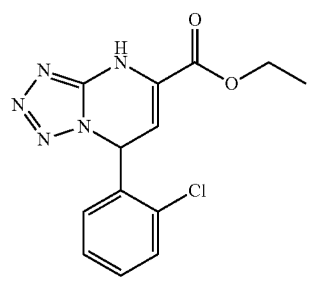 [SMILES: CCOC(=O)C1=CC(c2ccccc2Cl)n2nnnc2N1] | >300 | >300 | >300 | >300 | >300 |
| EJ3051 | 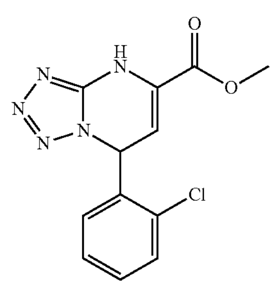 [SMILES: COC(=O)C1=CC(c2ccccc2Cl)n2nnnc2N1] | >300 | nd | nd | 100.6 | 102 |
| EJ3043 | 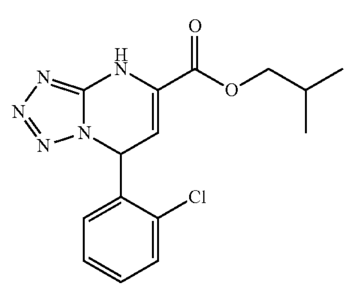 [SMILES: CC(C)COC(=O)C1=CC(c2ccccc2Cl)n2nnnc2N1] | >300 | >300 | >300 | >300 | >300 |

-continued

| Name | Structure | $K_i$ in FP (μM) | $IC_{50}$ HEp2 cells RSV (μM) | $CC_{50}$ HEp2 cells RSV (μM) | $IC_{50}$ BEAS2B cells RSV (μM) | $CC_{50}$ BEAS2B cells RSV (μM) |
|---|---|---|---|---|---|---|
| EJ3057 | 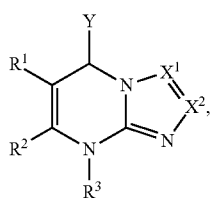 | >300 | nd | nd | 112 | >100 |
| EJ3054 | 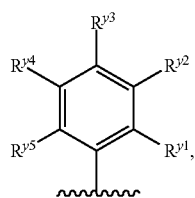 | >300 uM | nd | nd | 100.2 uM | 130.7 uM |

The invention claimed is:

1. A compound having the formula:

R¹—[structure with Y, X¹, X², N, R², R³]

or a pharmaceutically acceptable salt thereof, wherein:
$X^1$ is N;
$X^2$ is N;
Y is a phenyl group having the formula:

[phenyl structure with $R^{y1}$, $R^{y2}$, $R^{y3}$, $R^{y4}$, $R^{y5}$], wherein $R^{y2}$, $R^{y3}$, $R^{y4}$, and $R^{y5}$ are each hydrogen, and $R^{y1}$ is selected from F, Cl, Br, I, and $CF_3$;

$R^1$ is hydrogen;

$R^2$ is selected $C(O)OR^{2a}$ and $C(O)N(R^{2a})_2$, wherein $R^{2a}$ is in each case independently selected from , $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^3$ is hydrogen.

2. The compound according to claim 1, wherein $R^{y1}$ is $CF_3$.

3. The compound according to claim 1, wherein $R^2$ is $C(O)OR^{2a}$.

4. The compound according to claim 1, wherein $R^2$ is $C(O)OR^{2a}$ and $R^{2a}$ is $C_{1-8}$alkyl.

5. The compound according to claim 3, wherein $R^{y1}$ is Cl.

6. The compound according to claim 1, wherein $R^{y1}$ is F.

7. A pharmaceutical composition comprising the compound of claim 1.

8. A method of treating a patient infected with RSV, comprising administering the compound of claim 1.

9. The method of claim 8, further comprising administering adjunctively at least one other active compound.

* * * * *